(12) United States Patent
Wang et al.

(10) Patent No.: US 8,722,851 B2
(45) Date of Patent: May 13, 2014

(54) ANALGESIA WITH MINIMAL TOLERANCE AND DEPENDENCE BY A MU OPIOID RECEPTOR AGONIST THAT ALSO BINDS FILAMIN A

(75) Inventors: Hoau-Yan Wang, Philadelphia, PA (US); Lindsay Burns Barbier, Palo Alto, CA (US); Jian Wang, Groton, CT (US)

(73) Assignee: Pain Therapeutics, Inc., Austin, TX (US)

( * ) Notice: Subject to any disclaimer, the term of this patent is extended or adjusted under 35 U.S.C. 154(b) by 1040 days.

(21) Appl. No.: 12/263,257

(22) Filed: Oct. 31, 2008

(65) Prior Publication Data

US 2009/0191579 A1    Jul. 30, 2009

Related U.S. Application Data

(60) Provisional application No. 60/985,086, filed on Nov. 2, 2007.

(51) Int. Cl.
*C07K 14/00* (2006.01)
(52) U.S. Cl.
USPC ....................................................... 530/324
(58) Field of Classification Search
None
See application file for complete search history.

(56) References Cited

U.S. PATENT DOCUMENTS 7,026,443 B1 *    4/2006   Sette et al. .................... 530/300

\* cited by examiner

*Primary Examiner* — Christina Bradley
(74) *Attorney, Agent, or Firm* — Husch Blackwell, LLP

(57) ABSTRACT

A composition and method are disclosed that utilize an isolated polypeptide or analog thereof to inhibit the interaction of a mu-opioid receptor with filamin A. A contemplated polypeptide has an amino acid residue sequence illustrated by the formula: W-$[X_1X_2X_3 \ldots X_{43}X_{44}X_{45}]_n$ValAla$X_{48}$GlyLeu$[X_{51}X_{52}X_{53} \ldots X_{94}X_{95}X_{96}]_m$-Y, wherein the various elements are defined elsewhere. A contemplated method can be used to select a VAKGL-binding compound.

20 Claims, 21 Drawing Sheets

A7 cell membranes

M2 cell membranes

SEQUENCE LISTING

<160> NUMBER OF SEQ ID NOS: 17

<210> SEQ ID NO 1
<211> LENGTH: 45
<212> TYPE: PRT
<213> ORGANISM: Artificial Sequence
<220> FEATURE:
<223> OTHER INFORMATION: synthetic sequence

<400> SEQUENCE: 1

Val Thr Gly Pro Arg Leu Val Ser Asn His Ser Leu His Glu Thr Ser
1               5                   10                  15

Ser Val Phe Val Asp Ser Leu Thr Lys Ala Thr Cys Ala Pro Gln His
            20                  25                  30

Gly Ala Pro Gly Pro Gly Pro Ala Asp Ala Ser Lys Val
        35                  40                  45

```
<210> SEQ ID NO 2
<211> LENGTH: 45
<212> TYPE: PRT
<213> ORGANISM: Artificial sequence
<220> FEATURE:
<223> OTHER INFORMATION: synthetic sequence

<400> SEQUENCE: 2

Gly Leu Ser Lys Ala Tyr Val Gly Gln Lys Ser Ser Phe Thr Val Asp
1               5                   10                  15

Cys Ser Lys Ala Gly Asn Asn Met Leu Leu Val Gly Val His Gly Pro
            20                  25                  30

Arg Thr Pro Cys Glu Glu Ile Leu Val Lys His Val Gly
        35                  40                  45

<210> SEQ ID NO 3
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: X is any amino acid

<400> SEQUENCE: 3

Val Ala Xaa Gly Leu
1               5

<210> SEQ ID NO 4
<211> LENGTH: 95
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (48)..(48)
<223> OTHER INFORMATION: X is any amino acid

<400> SEQUENCE: 4

Val Thr Gly Pro Arg Leu Val Ser Asn His Ser Leu His Glu Thr Ser
1               5                   10                  15

Ser Val Phe Val Asp Ser Leu Thr Lys Ala Thr Cys Ala Pro Gln His
            20                  25                  30

Gly Ala Pro Gly Pro Gly Pro Ala Asp Ala Ser Lys Val Val Ala Xaa
        35                  40                  45

Gly Leu Gly Leu Ser Lys Ala Tyr Val Gly Gln Lys Ser Ser Phe Thr
    50                  55                  60

Val Asp Cys Ser Lys Ala Gly Asn Asn Met Leu Leu Val Gly Val His
65                  70                  75                  80

Gly Pro Arg Thr Pro Cys Glu Glu Ile Leu Val Lys His Val Gly
                85                  90                  95

<210> SEQ ID NO 5
<211> LENGTH: 50
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (48)..(48)
<223> OTHER INFORMATION: X is any amino acid

<400> SEQUENCE: 5
```

```
Val Thr Gly Pro Arg Leu Val Ser Asn His Ser Leu His Glu Thr Ser
1               5                   10                  15

Ser Val Phe Val Asp Ser Leu Thr Lys Ala Thr Cys Ala Pro Gln His
            20                  25                  30

Gly Ala Pro Gly Pro Gly Pro Ala Asp Ala Ser Lys Val Val Ala Xaa
        35                  40                  45

Gly Leu
    50
```

<210> SEQ ID NO 6
<211> LENGTH: 50
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: X is any amino acid

<400> SEQUENCE: 6

```
Val Ala Xaa Gly Leu Gly Leu Ser Lys Ala Tyr Val Gly Gln Lys Ser
1               5                   10                  15

Ser Phe Thr Val Asp Cys Ser Lys Ala Gly Asn Asn Met Leu Leu Val
            20                  25                  30

Gly Val His Gly Pro Arg Thr Pro Cys Glu Glu Ile Leu Val Lys His
        35                  40                  45

Val Gly
    50
```

<210> SEQ ID NO 7
<211> LENGTH: 50
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (26)..(26)
<223> OTHER INFORMATION: X is any amino acid

<400> SEQUENCE: 7

```
Leu Thr Lys Ala Thr Cys Ala Pro Gln His Gly Ala Pro Gly Pro Gly
1               5                   10                  15

Pro Ala Asp Ala Ser Lys Val Val Ala Xaa Gly Leu Gly Leu Ser Lys
            20                  25                  30

Ala Tyr Val Gly Gln Lys Ser Ser Phe Thr Val Asp Cys Ser Lys Ala
        35                  40                  45

Gly Asn
    50
```

<210> SEQ ID NO 8
<211> LENGTH: 45
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (23)..(23)
<223> OTHER INFORMATION: X is any amino acid

<400> SEQUENCE: 8

```
Ala Thr Cys Ala Pro Gln His Gly Ala Pro Gly Pro Gly Pro Ala Asp
```

```
                1               5                   10                  15
Ala Ser Lys Val Val Ala Xaa Gly Leu Gly Leu Ser Lys Ala Tyr Val
                        20                  25                  30

Gly Gln Lys Ser Ser Phe Thr Val Asp Cys Ser Lys Ala
            35                  40                  45

<210> SEQ ID NO 9
<211> LENGTH: 35
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (18)..(18)
<223> OTHER INFORMATION: X is any amino acid

<400> SEQUENCE: 9

Gln His Gly Ala Pro Gly Pro Gly Pro Ala Asp Ala Ser Lys Val Val
1               5                   10                  15

Ala Xaa Gly Leu Gly Leu Ser Lys Ala Tyr Val Gly Gln Lys Ser Ser
                20                  25                  30

Phe Thr Val
        35

<210> SEQ ID NO 10
<211> LENGTH: 25
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (13)..(13)
<223> OTHER INFORMATION: X is any amino acid

<400> SEQUENCE: 10

Gly Pro Gly Pro Ala Asp Ala Ser Lys Val Val Ala Xaa Gly Leu Gly
1               5                   10                  15

Leu Ser Lys Ala Tyr Val Gly Gln Lys
                20                  25

<210> SEQ ID NO 11
<211> LENGTH: 15
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (8)..(8)
<223> OTHER INFORMATION: X is any amino acid

<400> SEQUENCE: 11

Asp Ala Ser Lys Val Val Ala Xaa Gly Leu Gly Leu Ser Lys Ala
1               5                   10                  15

<210> SEQ ID NO 12
<211> LENGTH: 5
<212> TYPE: PRT
<213> ORGANISM: Artificial sequence
<220> FEATURE:
<223> OTHER INFORMATION: synthetic sequence

<400> SEQUENCE: 12

Val Ala Ala Gly Leu
1               5
```

```
<210> SEQ ID NO 13
<211> LENGTH: 5
<212> TYPE: PRT
<213> ORGANISM: Artificial sequence
<220> FEATURE:
<223> OTHER INFORMATION: synthetic sequence

<400> SEQUENCE: 13

Ala Ala Lys Gly Leu
 1               5

<210> SEQ ID NO 14
<211> LENGTH: 5
<212> TYPE: PRT
<213> ORGANISM: Artificial sequence
<220> FEATURE:
<223> OTHER INFORMATION: synthetic sequence

<400> SEQUENCE: 14

Val Ala Lys Gly Leu
 1               5

<210> SEQ ID NO 15
<211> LENGTH: 5
<212> TYPE: PRT
<213> ORGANISM: Artificial sequence
<220> FEATURE:
<223> OTHER INFORMATION: synthetic sequence

<400> SEQUENCE: 15

Val Ala Lys Ala Leu
 1               5

<210> SEQ ID NO 16
<211> LENGTH: 5
<212> TYPE: PRT
<213> ORGANISM: Artificial sequence
<220> FEATURE:
<223> OTHER INFORMATION: synthetic sequence

<400> SEQUENCE: 16

Val Ala Lys Gly Ala
 1               5

<210> SEQ ID NO 17
<211> LENGTH: 95
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(95)
<223> OTHER INFORMATION: The amino terminus of the protein sequence has
      a hydrogen or a C1-C20 acyl group.
<220> FEATURE:
<221> NAME/KEY: MISC_FEATURE
<222> LOCATION: (1)..(95)
<223> OTHER INFORMATION: Carboxy terminus has a hydroxyl group, an amino
      group, or a substituted amino group represented by -NR1R2.  R1 and
      R2 are independently hydrido, C1-C6 hydrocarbyl, amino C1-C6
      hydrocarbyl, hydroxy C1-C6 hydrocarbyl, aryl, aryl C1-C6
<220> FEATURE:
<221> NAME/KEY: MISC_FEATURE
<222> LOCATION: (1)..(95)
<223> OTHER INFORMATION: If Carboxy terminus has a substituted amino
      group represented by -NR1R2, R1 and R2 can form, together with the
      depicted nitrogen atom, a 5-8 membered ring containing zero or one
      aditional heteroatom that is oxygen, nitrogen or sulfur.
<220> FEATURE:
```

```
<221> NAME/KEY: MISC_FEATURE
<222> LOCATION: (1)..(45)
<223> OTHER INFORMATION: Amino acids 1-45 may or may not be present but
      when present, the one amino acid with a position number less than
      45 is present, each amino acid with a higher position number up to
      position number 45 is also present
<220> FEATURE:
<221> NAME/KEY: MISC_FEATURE
<222> LOCATION: (48)..(48)
<223> OTHER INFORMATION: X is any amino acid
<220> FEATURE:
<221> NAME/KEY: MISC_FEATURE
<222> LOCATION: (51)..(95)
<223> OTHER INFORMATION: Amino acids 51-95 may or may not be present but
      when present, the one amino acid with a position number greater
      than 51 is present, each amino acid with a lower position number
      down to position number 51 is also present

<400> SEQUENCE: 17

Val Thr Gly Pro Arg Leu Val Ser Asn His Ser Leu His Glu Thr Ser
1               5                   10                  15

Ser Val Phe Val Asp Ser Leu Thr Lys Ala Thr Cys Ala Pro Gln His
            20                  25                  30

Gly Ala Pro Gly Pro Gly Pro Ala Asp Ala Ser Lys Val Val Ala Xaa
        35                  40                  45

Gly Leu Gly Leu Ser Lys Ala Tyr Val Gly Gln Lys Ser Ser Phe Thr
50                  55                  60

Val Asp Cys Ser Lys Ala Gly Asn Asn Met Leu Leu Val Gly Val His
65                  70                  75                  80

Gly Pro Arg Thr Pro Cys Glu Glu Ile Leu Val Lys His Val Gly
                85                  90                  95
```

ANALGESIA WITH MINIMAL TOLERANCE AND DEPENDENCE BY A MU OPIOID RECEPTOR AGONIST THAT ALSO BINDS FILAMIN A

CROSS-REFERENCE TO RELATED APPLICATION

This applications claims priority from provisional application Ser. No. 60/985,086 that was filed on Nov. 2, 2007, and whose disclosures are incorporated herein by reference.

TECHNICAL FIELD

This invention contemplates a composition and related method for providing opioid-like analgesia while minimizing analgesic tolerance, physical dependence and addiction. More particularly, a composition and method are described that utilize an isolated polypeptide or small molecule to inhibit the interaction of the mu-opioid receptor with filamin A, either by binding to filamin A itself or by mimicking filamin A's binding to the mu opioid receptor. Preferably, the composition prevents this mu opioid receptor-filamin A interaction and also functions as a mu opioid receptor agonist.

BACKGROUND OF THE INVENTION

Opiates are powerful analgesics (agents used for the treatment of pain), but their use is hampered by non-trivial side effects, tolerance to the analgesic effects, physical dependence resulting in withdrawal effects, and by concerns surrounding the possibility of addiction. By itself, enhanced analgesic efficacy of an opiate can result in opioid sparing, and therefore a reduction in opioid-related side effects. The side effects of opiates include nausea, vomiting, pruritus, insomnia, constipation, sedation and impaired physical function (Ballantyne et al., 2003 *N Engl J Med* 349:1943-1953).

In many cases, patients taking opioids balance side effects with analgesia, often choosing to tolerate a certain amount of pain so as to avoid side effects. The more severe side effect of respiratory depression can also limit the tolerated dose, and hence the effective analgesia in many patients.

One of the most problematic aspects of opioid therapy is analgesic tolerance with prolonged treatment. Tolerance can be defined as the need for progressively higher doses in order to maintain the same reduction in pain. Although opioid rotation is currently used to minimize tolerance, this approach requires close monitoring due to variable cross-tolerance and side effect profiles among different patients (Fine, 2004 *J Pain Palliat Care Pharmacother* 18:75-79).

In its most severe form, opioid tolerance can manifest as opioid-induced hyperalgesia; that is, the opiate no longer reduces pain but actually increases or induces pain (Arner et al., 1988 *Acta Anaesthesiol Scan* 32:253-259; Simonnet et al., 2003 *Neuroreport* 14:1-7; Fine, 2004 *J Pain Palliat Care Pharmacother* 18:75-79). This hyperalgesia is clinically similar to the hyperalgesia of neuropathic pain, and in vivo models show that brainstem descending pain facilitation pathways are activated in both syndromes (Vanderah et al., 2001 *Pain* 92:5-9). Like neuropathic pain, opioid-induced hyperalgesia is extremely difficult to treat and is often a physician's greatest fear in initiating opioid therapy.

Dependence and addiction are also among the greatest fears of pain patients surrounding the use of opiates. Dependence is characterized by physical or psychological withdrawal upon discontinuation of the opiate and can be independent of addiction, which itself is defined by repeated, often self-destructive behaviors focused on obtaining the drug, according to DSM-IV criteria (American Psychiatric Association, 2000).

However, it is still thought that physical dependence, or the desire to avoid withdrawal, contributes to opiate addiction, particularly at later stages of addiction; whereas, a craving for the euphoric effects of opiates can dominate in earlier stages (Koob et al., 1989 *Neurosci Biobehav Rev* 13:135-140). The somatic withdrawal signs that can occur when opioid therapy is abruptly stopped in physically dependent individuals include agitation, irritability, muscular jerks, abdominal pain, diarrhea, burning sensations, "gooseflesh" and itching (Miser et al., 1986 *Am J Dis Child* 140:603-604; Heit, 2003 *J Pain Palliat Care Phamacother* 17:15-29).

Abrupt cessation of opioid treatment can also cause a hyperalgesia, which has also been referred to as opioid-induced hyperalgesia (Li et al., 2001 *Anesth Analg* 93:204-209). Although patients receiving prolonged opioid analgesic therapy can or can not develop analgesic tolerance, they usually become physically dependent, requiring careful tapering off of the opiate in order to minimize withdrawal effects (Heit, 2003 *J Pain Palliat Care Phamacother* 17:15-29; Woolf et al., 2004 *Curr Opin Investig Drugs* 5:61-66).

Opiates produce analgesia by activation of opioid receptors that belong to the superfamily of G protein-coupled receptors (GPCRs). Opioid receptors are also involved in the development of the physical and psychological dependence that are important aspects of drug abuse and addiction.

Studies on GPCRs, including opioid receptors, have shown that the third cytoplasmic loop and the carboxyl-terminal tail are very important for signal transduction (Law et al., 2000 *Annu Rev Pharmacol Toxicol* 40:389-430), regulation (Law and Loh, 1999 *J Pharmacol Exp Ther* 289:607-624), and internalization of GPCRs (Trapaidze et al., 1996 *J Biol Chem* 271:29279-29285; Keith et al., 1998 *Mol Pharmacol* 53:377-384), and are frequently involved in the association of the receptors with other proteins. In addition to G proteins, examples of proteins known to interact with GPCRs are Gprotein-coupled receptor kinases (Pitcher et al., 1998 *Annu Rev Biochem* 67:653-692), β-arrestins (Lefkowitz, 1998 *J Biol Chem* 273:18677-18680), PDZ domain-containing adaptor molecules (Milligan and White, 2001 *Trends Pharmacol Sci* 22:513-518), and scaffolding proteins such as filamin A (Onoprishvilli et al., 2003 *Molec Pharmacol* 64:1092-1100).

More specifically, opiates produce analgesia by activation of mu (μ) opioid receptor-linked inhibitory G protein signaling cascades and related ion channel interactions that suppress cellular activities by hyperpolarization. The μ opioid receptor (MOR) preferentially couples to pertussis toxin-sensitive G proteins, Gαi/o (inhibitory/other), and inhibits the adenylyl cyclase/cAMP pathway (Laugwitz et al., 1993 *Neuron* 10:233-242; Connor et al., 1999 *Clin Exp Pharmacol Physiol* 26:493-499). The analgesic effects of MOR activation have been predominantly attributed to the Gβγ dimer released from the Gαi/o protein, which activates G protein activated inwardly rectifying potassium (GIRK) channels (Ikeda et al., 2000 *Neurosci Res* 38:113-116) and inhibits voltage-dependent calcium channels (VDCCs) (Saegusa et al., 2000 *Proc Natl Acad Sci USA* 97:6132-6137), thereby suppressing cellular activities by hyperpolarization.

Adenylyl cyclase inhibition can also contribute to opioid analgesia, or its activation can contribute to analgesic tolerance. This inhibition is due to overexpression of adenylyl cyclase type 7 in the CNS of mice that leads to more rapid tolerance to morphine (Yoshimura et al., 2000 *Mol Pharmacol* 58:1011-1016). Additionally, adenylyl cyclase activation has been suggested to elicit analgesic tolerance or tolerance-associated hyperalgesia (Wang et al., 1997 *J Neurochem* 68:248-254). Although the superactivation of adenylyl cyclase after chronic opioid administration is more often viewed as a hallmark of opioid dependence than as a mediator of tolerance (Nestler, 2001 *Am J Addict* 10:201-217), both are consequences of chronic opioid administration, and tolerance often worsens dependence. Chronic pain patients who have escalated their opioid dose over time often experience more withdrawal than patients on a constant dose.

An important but underemphasized cellular consequence of chronic opioid treatment is excitatory signaling by opioid receptors in place of the usual inhibitory signaling (Crain et al., 1992 *Brain Res* 575:13-24; Crain et al., 2000 *Pain* 84:121-131; Gintzler et al., 2001 *Mol Neurobiol* 21:21-33; Wang et al., 2005 *Neuroscience* 135:247-261), possibly as a result of the decreased efficiency of coupling to the native G proteins; that decrease in efficiency being the index of desensitization (Sim et al., 1996 *J Neurosci* 16:2684-2692). Although the cellular effects of opiates are normally inhibitory, several in vitro studies have demonstrated that opiates can elicit excitatory effects either at low doses (Shen et al., 1989 *Brain Res* 491:227-242; Crain et al., 1990 *Trands Pharmaol Sci* 11:77-81) or after chronic exposure (Crain et al., 1992 *Brain Res* 575:13-24).

In vivo, opiates can cause "paradoxical hyperalgesia" at low doses (Kayser et al., 1987 *Brain Res* 414:155-157; Kiyatkin, 1989 *Int J Neurosci* 45:231-246; Crain et al., 2001 *Brain Res* 888:75-82), or after chronic administration, opioid-induced hyperalgesia (Arner et al., 1988 *Acta Anaesthesiol Scan* 32:253-259). Although descending facilitation of spinal cord dorsal horn neurons has been implicated in tolerance-associated hyperalgesia (Vanderah et al., 2001 *Pain* 92:5-9), alterations in opioid receptor signaling also occur with chronic opioid treatment (Shen et al., 1989 *Brain Res* 491: 227-242; Crain et al., 1990 *Trends Pharmacol Sci* 11:77-81; Crain et al., 1992 *Brain Res* 575:13-24; Gintzler et al., 2001 *Mol Neurobiol* 21:21-33) and can contribute to the enhanced firing of descending brainstem projections.

Chronic opioid treatment causes excitatory signaling of opioid receptors via a switch in their G protein coupling from Gi/o to Gs proteins (Wang et al 2005 *Neuroscience* 135:247-261; Chakrabarti et al., 2005 *Mol Brain Res* 135:217-224) and by stimulation of adenylyl cyclase II and IV by mu opioid receptor-associated Gβγ dimers (Chakrabarti et al., 1998 *Mol Pharmacol* 54:655-662; Wang et al., 2005 *Neuroscience* 135: 247-261). The interaction of the Gβγ dimer with adenylyl cyclase had previously been postulated to be the sole signaling change underlying the excitatory effects of opiates (Gintzler et al., 2001 *Mol Neurobiol* 21:21-33). It has further been shown that the Gβγ that interacts with adenylyl cyclases originates from the Gs protein coupling to MOR and not from the Gi/o proteins native to MOR (Wang et al., 2006 *J Neurobiol* 66:1302-1310). Importantly, the switch in G protein coupling by MOR and the interaction of the Gβγ dimer with adenylyl cyclase II and IV, are both signaling alterations attenuated by co-treatment of ultra-low-dose opioid antagonists, such as naloxone (NLX) or naltrexone (NTX), with opioid agonists (Wang et al., 2005 *Neuroscience* 135:247-261).

Ultra-low-dose opioid antagonists have been shown to enhance opioid analgesia, minimize opioid tolerance and dependence (Crain et al., 1995 *Proc Natl Acad Sci USA* 92:10540-10544; Powell et al. 2002. *JPET* 300:588-596), and attenuate the addictive properties of opioids (Leri et al., 2005 *Pharmacol Biochem Behav* 82:252-262; Olmstead et al., 2005 *Psychopharmacology* 181:576-581). An ultra-low dose of opioid antagonist was an amount initially based on in vitro studies of nociceptive dorsal root ganglion neurons and on in vivo mouse studies, wherein the amount of the excitatory opioid receptor antagonist administered is about 1000- to about 10,000,000-fold less, preferably about 10,000- to about 1,000,000-fold less than the amount of opioid agonist administered. It has long been hypothesized that ultra-low-dose opioid antagonists enhance analgesia and alleviate tolerance/dependence by blocking the excitatory signaling opioid receptors that underlie opioid tolerance and hyperalgesia (Crain et al., 2000 *Pain* 84:121-131).

The attenuation of analgesic tolerance by administration of ultra-low doses, defined herein after, of NLX has been demonstrated in rat studies, where rats treated with morphine and low doses of NLX showed no antinociceptive tolerance (or tolerance to reducing sensitivity to painful stimuli) when compared to rats treated with morphine alone. Signs of physical dependence were also markedly reduced when morphine was administered with ultra-low dosages of NLX. Antinociception (reducing sensitivity to painful stimuli) was not observed in rats administered NLX alone. Further, co-administration of morphine and NLX resulted in a marked reduction in MOR-Gs coupling associated with analgesic tolerance and dependence. The interaction of Gβγ with adenylyl cyclase II or IV was also markedly attenuated or abolished when rats were co-treated with morphine+NLX. These findings suggest that ultra-low-dose NLX reduces antinociceptive tolerance and dependence by preventing the mu opioid receptor-Gs coupling that results from the chronic opiate administration.

The development of novel therapeutics that combine ultra-low-dose opioid antagonists with opiates is currently under development in products such as Oxytrex™ (oxycodone plus ultra-low-dose NLX) from Pain Therapeutics, Inc (San Mateo, Calif.). The combination of ultra-low-dose opioid antagonists with opioid agonists formulated together in one medication has been shown to alleviate many of these undesirable aspects of opioid therapy (Burns, 2005 *Recent Developments in Pain Research* 115-136, ISBN:81-308-0012-8). This approach shows promise for an improvement in analgesic efficacy, and animal data suggests reduced addictive potential.

The need still remains for a deeper understanding of the cellular mechanism of action of ultra-low-dose opioid antagonists. Specifically, the identification of the cellular target of ultra-low-dose opioid antagonists in their inhibition of mu opioid receptor-Gs coupling can permit development of assays to screen as well as against this target to create a new generation of pain therapeutics that can provide long-lasting analgesia with minimal tolerance, dependence and addictive properties. Importantly, a non-opioid cellular target of ultra-low-dose NLX or NTX would provide potential for developing either a therapeutic combination of which one component is not required to be ultra-low-dose, or a single-entity novel analgesic.

The present invention identifies the precise target for such screening assays, and describes one such screening assay as well as the characteristics of potential single-entity drug candidates that provide strong opioid-like analgesia, while minimizing tolerance, dependence and addictive properties.

BRIEF SUMMARY OF THE INVENTION

The present invention contemplates a polypeptide, a polypeptide bound to a multicyclic ring system or a VAKGL-binding compound, defined herein after, an improved clinical and/or research composition containing that polypeptide or VAKGL-binding compound, or such polypeptide or VAKGL-binding compound that is also a mu opioid receptor agonist and a method of use thereof associated with the treatment of pain while minimizing or preventing opioid tolerance, dependence and addiction.

The present invention also contemplates novel VAKGL-binding compounds, defined herein after, that can inhibit MOR-Gs coupling through interactions with FLNA and/or the μ opioid receptor (MOR). In another aspect of the present invention, a polypeptide prevents the morphine-induced Gs protein coupling by MOR. That prevention of MOR-Gs coupling is believed to occur by preventing the interaction of filamin A and MOR. Downstream effects of preventing the MOR-Gs coupling include inhibition of cAMP accumulation and of CREB activation in a manner resembling the activity of ultra-low-dose opioid antagonists naloxone and naltrexone. In another aspect of the present invention, a polypeptide or VAKGL-binding compound will prevent the MOR-Gs coupling while itself activating MOR.

A contemplated polypeptide is an isolated polypeptide or analog thereof that contains up to 50 amino acid residues and comprises the amino acid sequence W-[$X_1X_2X_3 \ldots X_{43}X_{44}X_{45}$]$_n$-ValAlaX$_{48}$GlyLeu-[$X_{51}X_{52}X_{53} \ldots X_{94}X_{95}$]$_m$-Y [SEQ ID NO: 17], wherein W is hydrogen (hydrido) or a $C_1$-$C_{20}$ acyl group;

Y is a hydroxyl group, an amino group, or substituted amino group represented by —NR$^1$R$^2$, wherein R$^1$ and R$^2$ are independently selected from the group consisting of a hydrido, a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or R$^1$ and R$^2$ together with the depicted nitrogen atom form a 5- to 8-membered ring containing zero or one additional heteroatom that is oxygen, nitrogen, or sulfur;

X is an amino acid residue; and n and m are each independently zero or 1; wherein when n is zero, amino acid residues represented by positional subscripts as $X_1$ through $X_{45}$ are absent, and when n is 1, up to 45 residues of the amino acid sequence represented by SEQ. ID. NO:1 are present as amino acid residues $X_1$ through $X_{45}$, with the proviso that when one subscripted X residue with a position number less than 45 is present, each subscripted X reside with a higher subscript number up to 45 is also present. Similarly, when m is zero, amino acid residues represented by positional subscripts as $X_{51}$ through $X_{96}$ are absent and when m is 1, up to 45 residues of the amino acid sequence represented by SEQ. ID. NO:2 are present as amino acid residues $X_{51}$ through $X_{96}$, with the proviso that when one subscripted X residue with a position number greater than 51 is present, each subscripted X residue with a lower subscript number down to 51 is also present. The sum of n and m equals zero to 45.

Looked at differently, the above isolated polypeptide or analog thereof that contains up to 50 amino acid residues has the amino acid residue sequence of SEQ ID NO: 17 that is W-(Val Thr Gly Pro Arg Leu Val Ser Asn His Ser Leu His Glu Thr Ser Ser Val Phe Val Asp Ser Leu Thr Lys Ala Thr Cys Ala Pro Gln His Gly Ala Pro Gly Pro Gly Pro Ala Asp Ala Ser Lys Val)$_n$ Val Ala Xaa Gly Leu (Gly Leu Ser Lys Ala Tyr Val Gly Gln Lys Ser Ser Phe Thr Val Asp Cys Ser Lys Ala Gly Asn Asn Met Leu Leu Val Gly Val His Gly Pro Arg Thr Pro Cys Glu Glu Ile Leu Val Lys His Val Gly)$_m$-Y wherein W is hydrogen (hydrido) or a $C_1$-$C_{20}$ acyl group;

Y is a hydroxyl group, an amino group, or substituted amino group represented by —NR$^1$R$^2$, wherein R$^1$ and R$^2$ are independently selected from the group consisting of a hydrido, a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or R$^1$ and R$^2$ together with the depicted nitrogen atom form a 5- to 8-membered ring containing zero or one additional heteroatom that is oxygen, nitrogen, or sulfur;

Xaa is an amino acid residue;

n and m are each independently zero or 1, wherein when n is zero, amino acid residues within the parentheses are absent and when n is 1, up to 45 residues of the parenthesized amino acid sequence are present, with the proviso that when one of the residues within the parentheses is present, each residue to the carboxy-terminal side of said residue is also present in the sequence shown, and when m is zero, amino acid residues within the parentheses are absent, and when m is 1, up to 45 residues of the parenthesized amino acid sequence are present, with the proviso that when one of the residues within the parentheses is present, each residue to the amino-terminal side of said residue is also present in the sequence shown.

It is also to be understood that the ellipses in the above formula shown in sequences [$X_1X_2X_3 \ldots X_{43}X_{44}X_{45}$] and [$X_{51}X_{52}X_{53} \ldots X_{94}X_{95}X_{96}$] are meant to indicate that each of the undesignated amino acid residues $X_4$ through $X_{42}$ and can $X_{54}$ through $X_{93}$ be present, depending upon the values of "n" and "m", but are not shown simply as a matter of convenience of expression.

In one aspect of the invention, the amino acid residue $X_{48}$ in a before-defined polypeptide is a basic amino acid residue such as lysine, arginine or histidine. More preferably, $X_{48}$ is lysine.

In another aspect, a polypeptide of the invention is an isolated polypeptide of up to 50 amino acid residues contained within the amino acid sequence of SEQ. ID. NO:4, wherein the polypeptide contains at least the pentapeptide amino acid sequence Val-Ala-X-Gly-Leu of SEQ. ID. NO:3, wherein X is an amino acid residue.

In another aspect, a polypeptide of the invention is an isolated polypeptide of up to 50 amino acid residues containing at least a VAKGL-binding compound target amino acid sequence and is selected from the group comprising: SEQ. ID. NO:3, SEQ. ID. NO:5, SEQ. ID. NO:6, SEQ. ID. NO:7, SEQ. ID. NO:8, SEQ. ID. NO:9, SEQ. ID. NO:10, and SEQ. ID. NO:11.

In a further embodiment of the invention, a before-defined polypeptide of the formula W-[$X_1X_2X_3 \ldots X_{43}X_{44}X_{45}$]$_n$ValAlaX$_{48}$GlyLeU[$X_{51}X_{52}X_{53} \ldots X_{94}X_{95}$]$_m$-Y [SEQ ID NO:17] binds to a VAKGL-binding compound, wherein the VAKGL-binding compound interacts with FLNA and/or is an agonist of the mu opioid receptor and is selected from a group that can include, but is not limited to opioid antagonists naloxone and naltrexone.

In a further aspect of the invention, a before-defined polypeptide of the formula W-[$X_1X_2X_3 \ldots X_{43}X_{44}X_{45}$]$_n$ValAlaX$_{48}$GlyLeu[$X_{51}X_{52}X_{53} \ldots X_{94}X_{95}X_{96}$]$_m$-Y binds to a VAKGL-binding compound and a mu opioid receptor, wherein the binding affinity of the VAKGL-binding compound is 20 fold greater for the polypeptide than the binding affinity of the VAKGL-binding compound for the μ-opioid receptor.

In another embodiment, the invention contemplates a method for screening a candidate VAKGL-binding compound that binds to an isolated polypeptide that includes at least the amino acid sequence Val-Ala-X-Gly-Leu (SEQ ID NO:3). That polypeptide is filamin A (FLNA) or an analog thereof having the amino acid sequence of SEQ. ID. NO:4, wherein X is an amino acid residue, comprising the steps of: (a) contacting the candidate VAKGL-binding compound with the polypeptide in an aqueous medium; (b) maintaining the contact for a time period sufficient for the candidate VAKGL-binding compound and the polypeptide to bind to each other; and (c) determining the binding of the candidate VAKGL-binding compound to the polypeptide.

In another aspect of the invention, the above method utilizes an isolated polypeptide or analog thereof containing up to 50 amino acid residues comprising a before-defined amino acid sequence W-[$X_1X_2X_3$ . . . $X_{43}X_{44}X_{45}$]$_n$-ValAla$X_{48}$GlyLeu-[$X_{51}X_{52}X_{53}$...$X_{94}X_{95}X_{96}$]$_m$-Y [SEQ ID NO: 17].

In another embodiment, the invention contemplates a method for determining the ability of a candidate VAKGL-binding compound, other than naloxone or naltrexone, to inhibit the interaction of the mu-opioid receptor with filamin A and thereby prevent the mu opioid receptor from coupling to Gs proteins (Gs), comprising the steps of: (a) admixing an opioid agonist and the candidate VAKGL-binding compound with mammalian cells that contain the mu opioid receptor and filamin A (FLNA) in their native conformations and relative orientations, the opioid agonist being present in an agonist effective amount and/or being administered in a repeated, chronic manner the VAKGL-binding compound being present in an FLNA-binding effective amount, defined herein after; and (b) determining inhibition of the interaction of the mu-opioid receptor with the G protein by analysis of the presence or the absence of the Gαs subunit of Gs protein, wherein the absence of the Gαs subunit indicates inhibition of the interaction of the mu-opioid receptor with the Gs protein.

In an alternate embodiment, the invention contemplates a method for determining the ability of an isolated polypeptide to interfere with candidate VAKGL-binding-compound-induced inhibition of the interaction of a mu-opioid receptor with filamin A and thereby prevent the mu opioid receptor from coupling to Gs proteins (Gs), comprising the steps of: (a) admixing an opioid agonist and the candidate VAKGL-binding compound with mammalian cells or CNS tissue cultures that contain the mu opioid receptor and filamin A (FLNA) in their native conformations or relative orientations, the opioid agonist being present in an agonist effective amount and/or being administered in a repeated, chronic manner and the VAKGL-binding compound being present in an FLNA-binding effective amount; (b) admixing an isolated polypeptide with the mammalian cells or CNS tissue cultures, the polypeptide containing up to 50 amino acid residues and comprising a before-defined amino acid sequence W-[$X_1X_2X_3$ . . . $X_{43}X_{44}X_{45}$]$_n$-ValAla$X_{48}$GlyLeu[$X_{51}X_{52}X_{53}$ . . . $X_{94}X_{95}$]$_m$-Y [SEQ ID NO: 17]; and (c) determining the presence of candidate VAKGL-binding compound-induced inhibition by analysis of the presence or the absence of the Gαs subunit, wherein the presence of inhibition indicates a failure of the polypeptide to interfere with candidate opioid antagonist-induced inhibition of the interaction of the mu opioid receptor with the Gs protein.

In another embodiment, the invention contemplates a method for inhibiting the interaction of a mu opioid receptor with a Gs protein that contains a Gαs subunit, comprising the steps of: (a) admixing an opioid agonist with mammalian cells that contain the mu-opioid receptor and filamin A (FLNA) in their native conformations or relative orientations, the opioid agonist being present in an agonist effective amount and/or administered in a repeated, chronic manner; (b) admixing an FLNA-binding effective amount of an isolated polypeptide with the mammalian cells or CNS tissue cultures, the polypeptide containing up to 50 amino acid residues comprising a before-defined amino acid sequence W-[$X_1X_2X_3$ . . . $X_{43}X_{44}X_{45}$]$_n$-ValAla$X_{48}$GlyLeu[$X_{51}X_{52}X_{53}$ . . . $X_{94}X_{95}$]$_m$-Y [SEQ ID NO: 17]; and (c) determining the inhibition by analysis of the presence or the absence of the Gαs subunit, wherein the absence of the Gαs subunit indicates inhibition of the interaction of the mu-opioid receptor with the Gs protein.

An additional aspect of the invention is a method for selecting a compound for VAKGL-binding activity that preferably also possesses mu opioid receptor agonist activity, from candidate compounds. That method comprises the steps of: a) determining the aromatic/hydrophobic and hydrogen bond acceptor functions and the distances there between of a candidate compound; and b) selecting a compound that exhibits at least three of the pharmacophores shown in FIGS. 12-27. A selected VAKGL-binding compound can bind to the VAKGL-binding site of filamin A alone, but will preferably also be an agonist at the mu-opioid receptor. A selected compound preferably exhibits at least six of the sixteen pharmacophores, more preferably at least nine of those pharmacophores, and most preferably at least twelve of the sixteen pharmacophores.

ABBREVIATIONS AND SHORT FORMS

The following abbreviations and short forms are used in this specification.

"MOR" means µ-opioid receptor
"FLNA" means filamin A
"NLX" means naloxone
"NTX" means naltrexone
"Gαi/o" means G protein alpha subunit-inhibitory/other conformation, inhibits adenylyl cyclase
"Gαs" means G protein alpha subunit-stimulatory conformation stimulates adenylyl cyclase
"Gβγ" means G protein beta gamma subunit
"cAMP" means cyclic adenosine monophosphate
"CREB" means cAMP Response Element Binding protein
"IgG" means Immunoglobulin G

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "polypeptide" refers to linear or cyclic or branched compounds containing amino acid residues, amino acid residue equivalents or other non-amino groups, while still retaining the desired functional activity of a peptide. Even though, the term "peptide" is used for a shorter sequence of amino acid residues, the words "polypeptide" and "peptide" are used interchangeably herein for ease of expression. Peptide equivalents can differ from conventional peptides by the replacement of one or more amino acid residues with related organic acids such a p-aminobenzoic acid (PABA), amino acid residue analogs, or the substitution or modification of side chains or functional groups. Peptide equivalents encompass peptide mimetics or peptidomimetics, which are organic molecules that retain similar peptide chain pharmacophore groups as are present in the corresponding peptide, but are linked together by other than a peptide bond. The term "peptide" refers to peptide equivalents as well as peptides.

It is to be understood that limited modifications can be made to a peptide without destroying its biological function. Thus, modifications of the peptides of the present invention that do not completely destroy their ability to bind opioid antagonists with high affinity are within the definition of the compounds claimed as such. Modifications can include, for example, additions, deletions, or substitutions of amino acid residues; substitutions of compounds that mimic amino acid residue structure or function; as well as the addition of chemical moieties such as amino or acetyl groups.

As used herein, each "amino acid residue" is represented by the full name thereof, by the three letter code corresponding thereto, or by the one-letter code corresponding thereto, as known to one of ordinary skill in the art. The term "amino acid residue" as used herein is meant to include standard, nonstandard amino acid residues, and both D and L amino acid residues. The term "standard" means any of the twenty standard L-amino acid residues commonly found in naturally occurring peptides. The term "nonstandard" amino acid residues means any amino acid residue, other than the standard amino acid residue that can be either derived from a natural source or prepared synthetically or a chemically modified amino acid, including but not limited to salts, amino acid derivatives (such as amides), and substitutions. Amino acid residues contained within the peptides of the invention, and particularly the amino acid residues at the carboxy- or amino-terminus, can be modified by methylation, amidation, acetylation or substitution with other chemical groups which can change the peptides' half life without adversely affecting their activity.

As used herein, the term "basic amino acid residue" refers to an amino acid that has a side chain that can be protonated and positively charged at pH values below and/or at physiological levels, e.g., pH 7.2-7.4. Examples of basic amino acid residues include, but are not limited to lysine, arginine and histidine.

As used herein, the term "hydrocarbyl" is a short hand term to include straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. Where a specific aliphatic hydrocarbyl substituent group is intended, that group is recited; i.e., $C_1$-$C_4$ alkyl, methyl or dodecenyl. Exemplary hydrocarbyl groups contain a chain of 1 to about 12 carbon atoms, and preferably one to about 10 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, isoamyl, hexyl, octyl, decyl, dodecyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. On the other hand, a hydrocarbyl group containing a —C(O)O— functionality is referred to as a hydrocarboyl group inasmuch as there is no ambiguity in using that suffix. As a skilled worker will understand, a substituent that cannot exist such as a $C_1$ alkenyl group is not intended to be encompassed by the word "hydrocarbyl".

The term "aryl", alone or in combination, means a phenyl or naphthyl radical that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O— arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

As used herein, the term "binds" refers to the adherence of molecules to one another, such as, but not limited to, peptides of the before-defined formula W-$[X_1X_2X_3 \ldots X_{43}X_{44}X_{45}]_n$-ValAla$X_{48}$GlyLeu$[X_{51}X_{52}X_{53} \ldots X_{94}X_{95}]_m$-Y [SEQ ID NO: 17] to VAKGL-binding compounds or opioid antagonists, such as naloxone or naltrexone.

As used herein, the term "selectively binds" refers to binding as distinct activities, in that a polypeptide of the before-defined formula W-$[X_1X_2X_3 \ldots X_{43}X_{44}X_{45}]_n$-ValAla$X_{48}$GlyLeu$[X_{51}X_{52}X_{53} \ldots X_{94}X_{95}]_m$Y [SEQ ID NO:17] can independently bind to a VAKGL-binding compound and a μ-opioid receptor, wherein the binding of the polypeptide to a VAKGL-binding compound and the binding of the polypeptide to a μ opioid receptor are two distinct events that can occur independently of one another.

As used herein, the term "binding affinity" refers to the interaction between a before-defined peptide of the formula W-$[X_1X_2X_3 \ldots X_{43}X_{44}X_{45}]_n$-ValAla$X_{48}$GlyLeu$[X_{51}X_{52} X_{53} \ldots X_{94}X_{95}]_m$-Y [SEQ ID NO:17] and its target binding site, for example, the binding of the peptide to a VAKGL-binding compound, an opioid antagonist or to a μ opioid receptor. In a related use, the term "antibody affinity" refers to the strength with which an antibody molecule binds an epitope or antigenic determinant. The binding affinity and the antibody affinity can be quantified by determining an association constant.

As used herein, the term "paratope containing portion" refers to a paratope as an idiotope or antigenic site of an antibody that is responsible for that antibody binding to an epitope or antigenic determinant. The term "epitope" refers to that part of an antigenic molecule to which the T-cell receptor response, a site on a molecule against which an antibody will be produced and to which it will bind. The paratope-containing portions (antibody combining sites or idiotypes) of antibodies are those portions of antibody molecules that include the idiotope, and bind to a before-defined peptide of the formula W-$[X_1X_2X_3 \ldots X_{43}X_{44}X_{45}]_n$ValAla$X_{48}$GlyLeu-$[X_{51}X_{52}X_{53} \ldots X_{94}X_{95}]_m$-Y [SEQ ID NO:17]. Such portions include the Fab, Fab', Fv and $F(ab')_2$ fragments prepared from antibodies by well-known enzymatic cleavage techniques. See for example, U.S. Pat. No. 4,342,566 to Theofilopoulos and Dixon, generally, and specifically, Pollack et al., *Science* 1987 234:1570, who reported accelerated hydrolytic rates for Fab fragments were the same as those of the native immunoglobulin. Inasmuch as the antibodies from which paratope-containing portions are obtained are described as raised against or induced by immunogens, paratope-containing (antibody combining site-containing) antibodies can also be discussed as being "raised" or "induced" with the understanding that a cleavage step is typically required to obtain only a paratope-containing polyamide from an antibody.

The antibodies useful in the present invention are monoclonal antibodies and polyclonal antibodies. A "monoclonal antibody" is a term in reference to an antibody produced by clones of a single cell called a hybridoma that secretes but one kind of antibody molecule. The hybridoma cell is fused from an antibody-producing cell and a myeloma cell or other self-perpetuating cell line. A "polyclonal antibody" is a term in reference to an antibody produced from different B-cell lines and is a mixture of immunoglobulin molecules secreted against a specific antigen, each recognizing a different epitope. The polyclonal antibody can be produced by immunization of a suitable mammal with an antigen to induce B-lymphocytes to produce IgG immunoglobulins specific for the antigen. The IgG immunoglobulins are then purified from the mammal's serum.

As used herein, the term "VAKGL-binding compound" refers to a compound that binds to the novel polypeptide or analog thereof encompassed by the present invention and represented by a before-defined peptide of the formula W-$[X_1X_2X_3 \ldots X_{43}X_{44}X_{45}]_n$-ValAla$X_{48}$GlyLeu$[X_{51}X_{52}X_{53} \ldots X_{94}X_{95}]_m$-Y [SEQ ID NO:17], wherein $X_{48}$ is preferably a basic amino acid and more preferably a lysine resulting in the polypeptide comprising residues -Val-Ala-Lys-Gly-Leu- or a VAKGL (SEQ ID NO:14) sequence. A VAKGL-binding compound can inhibit the MOR-Gs coupling caused by the interaction between an opioid agonist and the μ opioid receptor via interactions with filamin A in the $24^{th}$ repeat region. When co-administered with an opioid agonist, a VAKGL-binding compound in an ultra-low amount or higher amount can enhance the analgesic effects and improve the treatment of pain. If the VAKGL-binding compound both interacts with FLNA and is an agonist at the μ opioid receptor, the administration amount need not be an ultra-low amount, but rather is an analgesically effective amount.

As used herein, the term "candidate VAKGL-binding compound" refers to a substance to be screened as a potential VAKGL-binding compound. In preferred instances a VAKGL-binding compound is also an opioid agonist. Additionally, a VAKGL-binding compound can function in a combinatory manner similar to the combination of an opioid agonist and ultra-low-dose antagonist, wherein both FLNA and the mu-opioid receptor are targeted by a single-entity.

As used herein, the term "opioid receptor" refers to a G protein coupled receptor, located in the central nervous system that interacts with opioids. More specifically, the μ opioid receptor is activated by morphine causing analgesia, sedation, nausea, and many other side effects known to one of ordinary skill in the art.

As used herein, the term "opioid agonist" refers to a substance that upon binding to an opioid receptor can stimulate the receptor, induce G protein coupling and trigger a physiological response. More specifically, an opioid agonist is a morphine-like substance that interacts with MOR to produce analgesia.

As used herein, the term "opioid antagonist" refers to a substance that upon binding to an opioid receptor inhibits the function of an opioid agonist by interfering with the binding of the opioid agonist to the receptor.

As used herein an "agonist effective amount" refers to an amount sufficient to perform the functions described herein, such as activating MOR and eliciting a physiological response of analgesia: MOR-Gi/o protein coupling, inhibition of cAMP production, and any other cellular responses caused by the interaction of an opioid agonist and MOR that are known to one of ordinary skill in the art.

As used herein the term "ultra-low-dose" or "ultra-low amount" refers to an amount of compound that when given in combination with an opioid agonist is sufficient to enhance the analgesic potency of the opioid agonist. More specifically, the ultra-low-dose of an opioid antagonist admixed with an opioid agonist in mammalian cells is an amount about 1000- to about 10,000,000-fold less, and preferably between about 10,000- and to about 1,000,000-fold less than the amount of opioid agonist.

As used herein an "FLNA-binding effective amount" refers to an amount sufficient to perform the functions described herein, such as inhibition of MOR-Gs coupling, prevention of the cAMP desensitization measure, inhibition of CREB $S^{133}$ phosphorylation and inhibition of any other cellular indices of opioid tolerance and dependence, which functions can also be ascribed to ultra-low-doses of certain opioid antagonists such as naloxone or naltrexone. When a polypeptide or VAKGL-binding compound of the invention interacts with FLNA, an FLNA-binding effective amount can be an ultra-low amount or an amount higher than an ultra-low-dose as the polypeptide or VAKGL-binding compound will not antagonize the opioid receptor and compete with the agonist, as occurs with known opioid antagonists such as naloxone or naltrexone in amounts greater than ultra-low-doses. More preferably, when a polypeptide or VAKGL-binding compound of the present invention both interacts with FLNA and is an agonist of the mu opioid receptor, an FLNA-binding effective amount is an amount higher than an ultra-low-dose and is a sufficient amount to activate the mu opioid receptor.

As used herein the phrase "determining inhibition of the interaction of a mu opioid receptor with a Gs protein" refers to monitoring the cellular index of opioid tolerance and dependence generated from chronic or high-dose administration of opioid agonists to mammalian cells. More specifically, the mu opioid receptor-Gs coupling response can be identified by measuring the presence of the Gαs (stimulatory) subunit, the interaction of MOR with the G protein complexes and formation of Gs-MOR coupling, the interaction of the Gβγ protein with adenylyl cyclase types II and IV, loss of inhibition or outright enhancement of cAMP accumulation, and the activation of CREB via phosphorylation of $S^{133}$.

As used herein the term "naloxone/naltrexone positive control" refers to a positive control method comprising steps (a) through (c) discussed in the method embodiments above, wherein the candidate VAKGL-binding compound is a known opioid antagonist administered in an ultra-low amount, preferably naloxone or naltrexone.

As used herein the term "VAKGL-binding compound negative control" refers to a negative control method comprising steps (a) through (c) discussed in the method embodiments above, wherein the candidate VAKGL-binding compound is absent and the method is carried out in the presence of only opioid agonist and optionally, a before-defined peptide of the formula W-$[X_1X_2X_3 \ldots X_{43}X_{44}X_{45}]_n$-ValAla$X_{48}$GlyLeu$[X_{51}X_{52}X_{53} \ldots X_{94}X_{95}]_m$-Y [SEQ ID NO:17].

As used herein the term "pharmacophore" is not meant to imply any pharmacological activity. The term refers to chemical features and their distribution in three-dimensional space that constitutes and epitomizes the preferred requirements for molecular interaction with a receptor (U.S. Pat. No. 6,034,066).

BRIEF DESCRIPTION OF THE DRAWINGS

In the drawings forming a portion of this disclosure,

FIG. 1, in parts 1A trough 1H, identifies Filamin A (FLNA) as the protein binding to NLX in MOR immunoprecipitates; Western blot analysis (FIG. 1A; FIG. 1B), densitometric quantitation (FIG. 1C and FIG. 1D), whereas FIGS. 1E-1H illustrate an absence of binding of protein-specific antibodies to cytoskeletal proteins.

DETAILED DESCRIPTION OF THE INVENTION

Figure 1A:
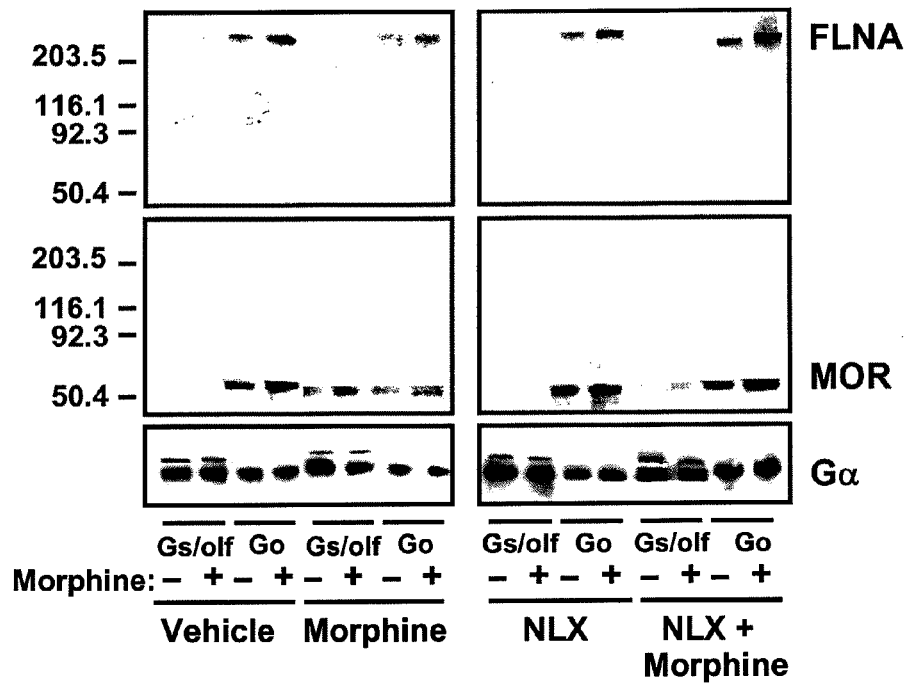

Each of the patents, patent applications and articles cited herein is incorporated by reference. The use of the article "a" or "an" is intended to include one or more.

Although the present invention is susceptible of embodiment in various forms, there is shown in the drawings a number of presently preferred embodiments that are discussed in greater detail hereafter. It should be understood that the present disclosure is to be considered as an exemplification of the present invention, and is not intended to limit the invention to the specific embodiments illustrated. It should be further understood that the title of this section of this application ("Detailed Description of the Invention") relates to a requirement of the United States Patent Office, and should not be found to limit the subject matter disclosed herein.

The present invention contemplates a polypeptide, a polypeptide bound to a multicyclic ring system or a VAKGL-binding compound, defined herein after, an improved clinical and/or research composition containing that polypeptide or VAKGL-binding compound, or such polypeptide or VAKGL-binding compound that is also a mu opioid receptor agonist and a method of use thereof associated with the treatment of pain while minimizing or preventing opioid tolerance, dependence and addiction.

The present invention also contemplates novel VAKGL-binding compounds, defined herein after, that can inhibit MOR-Gs coupling through interactions with FLNA and/or the μ opioid receptor (MOR). In another aspect of the present invention, a polypeptide prevents the morphine-induced Gs protein coupling by MOR. That prevention of MOR-Gs coupling is believed to occur by preventing the interaction of filamin A and MOR. Downstream effects of preventing the MOR-Gs coupling include inhibition of cAMP accumulation and of CREB activation in a manner resembling the activity of ultra-low-dose opioid antagonists naloxone and naltrexone. In another aspect of the present invention, a polypeptide or VAKGL-binding compound will prevent the MOR-Gs coupling while itself activating MOR.

A contemplated polypeptide is an isolated polypeptide or analog thereof that contains up to 50 amino acid residues and comprises the amino acid sequence W-[$X_1X_2X_3$ . . . $X_{43}X_{44}X_{45}$]$_n$-ValAlaX$_{48}$GlyLeu[$X_{51}X_{52}X_{53}$...$X_{94}X_{95}$]$_m$-Y [SEQ ID NO: 17], wherein W is hydrogen (hydrido) or a $C_1$-$C_{20}$ acyl group;

Y is a hydroxyl group, an amino group, or substituted amino group represented by —NR$^1$R$^2$, wherein R$^1$ and R$^2$ are independently selected from the group consisting of a hydrido (—H), a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or R$^1$ and R$^2$ together with the depicted nitrogen atom form a 5- to 8-membered ring containing zero or one additional heteroatom that is oxygen, nitrogen, or sulfur;

X is an amino acid residue; and n and m are each independently zero or 1; wherein when n is zero, amino acid residues represented by positional subscripts as $X_1$ through $X_{45}$ are absent and when n is 1, up to 45 residues of the amino acid sequence naturally present from residue 2516 through 2560 of human filamin A [UniProtKB/Swiss-Prot entry P21333, FLNA-HUMAN, Filamin-A protein sequence]represented by SEQ. ID. NO:1 are present as amino acid residues $X_1$ through $X_{45}$, with the proviso that when one subscripted X residue with a position number less than 45 is present, each subscripted X reside with a higher subscript number up to 45 is also present. Similarly, when m is zero, amino acid residues represented by positional subscripts as $X_{51}$ through $X_{96}$ are absent and when m is 1, up to 45 residues of the amino acid sequence naturally present from residue 2565 through 2615 of human filamin A [UniProtKB/ Swiss-Prot entry P21333, FLNA-HUMAN, Filamin-A protein sequence] represented by SEQ. ID. NO:2 are present as amino acid residues $X_{51}$ through $X_{96}$, with the proviso that when one subscripted X residue with a position number greater than 51 is present, each subscripted X residue with a lower subscript number down to 51 is also present. The sum of n and m equals zero to 45.

The above sequence of an isolated polypeptide or analog thereof that contains up to 50 amino acid residues can also be expressed as the amino acid residue sequence of SEQ ID NO: 17 that is W-(Val Thr Gly Pro Arg Leu Val Ser Asn His Ser Leu His Glu Thr Ser Ser Val Phe Val Asp Ser Leu Thr Lys Ala Thr Cys Ala Pro Gln His Gly Ala Pro Gly Pro Gly Pro Ala Asp Ala Ser Lys Val)$_n$ Val Ala Xaa Gly Leu (Gly Leu Ser Lys Ala Tyr Val Gly Gln Lys Ser Ser Phe Thr Val Asp Cys Ser Lys Ala Gly Asn Asn Met Leu Leu Val Gly Val His Gly Pro Arg Thr Pro Cys Glu Glu Ile Leu Val Lys His Val Gly)$_m$-Y wherein W is hydrogen (hydrido) or a $C_1$-$C_{20}$ acyl group;

Y is a hydroxyl group, an amino group, or substituted amino group represented by —$NR^1R^2$, wherein $R^1$ and $R^2$ are independently selected from the group consisting of a hydrido, a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or $R^1$ and $R^2$ together with the depicted nitrogen atom form a 5- to 8-membered ring containing zero or one additional heteroatom that is oxygen, nitrogen, or sulfur;

Xaa is an amino acid residue;

n and m are each independently zero or 1, wherein when n is zero, amino acid residues within the parentheses are absent and when n is 1, up to 45 residues of the parenthesized amino acid sequence are present, with the proviso that when one of the residues within the parentheses is present, each residue to the carboxy-terminal side of said residue is also present in the sequence shown, and when m is zero, amino acid residues within the parentheses are absent, and when m is 1, up to 45 residues of the parenthesized amino acid sequence are present, with the proviso that when one of the residues within the parentheses is present, each residue to the amino-terminal side of said residue is also present in the sequence shown.

```
                                           (SEQ. ID. NO: 1)
VTGPRLVSNHSLHETSSVFVDSLTKATCAPQHGAPGPGPADASKV, (SEQ. ID. NO: 2)
GLSKAYVGQKSSFTVDCSKAGNNMLLVGVHGPRTPCEEILVKHVG.
```

In one aspect of the invention, the amino acid residue $X_{48}$ in a before-defined polypeptide is a basic amino acid residue such as lysine, arginine or histidine. Preferably, $X_{48}$ is lysine.

In another aspect of the invention, the isolated polypeptide is a pentapeptide amino acid sequence wherein, the peptide W-[$X_1X_2X_3$ . . . $X_{43}X_{44}X_{45}$]$_n$-ValAlaX$_{48}$GlyLeU[$X_{51}X_{52}X_{53}$ . . . $X_{94}X_{95}$]$_m$-Y contains hydrogen at position W, a hydroxyl group at position Y and a lysine for X at position three, and n and m are both zero.

In another aspect, a polypeptide of the invention is an isolated polypeptide of up to 50 amino acid residues contained within the amino acid sequence of SEQ. ID. NO:4, wherein the polypeptide contains at least the pentapeptide amino acid sequence Val-Ala-X-Gly-Leu of SEQ. ID. NO:3, wherein X is an amino acid residue.

```
VAXGL (SEQ. ID. NO: 3):

VTGPRLVSNHSLHETSSVFVDSLTKATCAPQHGAPGPGPADAS
KVVAXGLGLSKAYVGQKSSFTVDCSKAGNNMLLVGVHGPRTPC
EEILVKHVG. (SEQ. ID. NO: 4)
```

In another aspect, a polypeptide of the invention is an isolated polypeptide of up to 50 amino acid residues containing at least a VAKGL-binding compound target amino acid sequence and is selected from the group comprising:

```
                                           (SEQ. ID. NO: 3)
VAXGLE, (SEQ. ID. NO: 5)
VTGPRLVSNHSLHETSSVFVDSLTKATCAPQHGAPGPGPADAS
KV, (SEQ. ID. NO: 6)
VAXGLGLSKAYVGQKSSFTVDCSKAGNNMLLVGVHGPRTPCEE
ILVKHVG, (SEQ. ID. NO: 7)
LTKATCAPQHGAPGPGPADASKVVAXGLGLSKAYVGQKSSFTV
DCSKAGN, (SEQ. ID. NO: 8)
ATCAPQHGAPGPGPADASKVVAXGLGLSKAYVGQKSSFTVDCS
KA, (SEQ. ID. NO: 9)
QHGAPGPGPADASKVVAXGLGLSKAYVGQKSSFTV, (SEQ. ID. NO: 10)
GPGPADASKVVAXGLGLSKAYVGQK,
and (SEQ. ID. NO: 11)
DASKVVAXGLGLSKA
```

In yet another embodiment of the invention, a before-defined polypeptide of the formula W-[$X_1X_2X_3$ . . . $X_{43}X_{44}X_{45}$]$_n$ValAlaX$_{48}$GlyLeu[$X_{51}X_{52}X_{53}$ . . . $X_{94}X_{95}$]$_m$-Y [SEQ ID NO:17] comprises standard (usual) L-amino acid residues. In a further aspect, at least one amino acid residue is a non-standard amino acid residue, defined hereinafter, a D-amino acid residue or a synthetic amino acid residue, defined herein after.

In an additional embodiment of the invention, a before-defined polypeptide of the formula W-[$X_1X_2X_3$ . . . $X_{43}X_{44}X_{45}$]$_n$ValAlaX$_{48}$GlyLeu-[$X_{51}X_{52}X_{53}$ . . . $X_{94}X_{95}$ $X_{96}$]$_m$-Y is a cyclic polypeptide synthesized from cyclic messenger RNA display with a trillion member covalent peptide macrocycle library to target the proteins, such as FLNA and MOR, with which the polypeptide interacts following the methods similar to Millward et al. 2007 *ACS Chemical Biology* 2(9):625-634.

In a further embodiment of the invention, a before-defined polypeptide of the formula W-[$X_1X_2X_3$ . . . $X_{43}X_{44}X_{45}$]$_n$ ValAlaX$_{48}$GlyLeU[$X_{51}X_{52}X_{53}$ . . . $X_{94}X_{95}$]$_m$-Y [SEQ ID NO:17] binds to a VAKGL-binding compound, wherein the VAKGL-binding compound interacts with FLNA and/or is an agonist of the mu opioid receptor and is selected from a group that can include, but is not limited to opioid antagonists naloxone and naltrexone.

In another aspect of the invention, a before-defined polypeptide of the formula W-[$X_1X_2X_3$ . . . $X_{43}X_{44}X_{45}$]$_n$ ValAlaX$_{48}$GlyLeu[$X_{51}X_{52}X_{53}$ . . . $X_{94}X_{95}$]$_m$-Y [SEQ ID NO:17]binds to a mu opioid receptor.

In yet another aspect of the invention, a before-defined polypeptide of the formula W-[$X_1X_2X_3$ . . . $X_{43}X_{44}X_{45}$]$_n$ ValAlaX$_{48}$GlyLeu[$X_{51}X_{52}X_{53}$ . . . $X_{94}X_{95}$]$_m$-Y [SEQ ID NO:17] binds to a VAKGL-binding compound, wherein the VAKGL-binding compound has a binding affinity for the polypeptide of about $5e^{-10}$ M to about $5e^{-12}$ M, preferably $5e^{-11}$ M.

In a further aspect of the invention, a before-defined polypeptide of the formula W-$[X_1X_2X_3 \ldots X_{43}X_{44}X_{45}]_n$ValAla$X_{48}$GlyLeu-$[X_{51}X_{52}X_{53} \ldots X_{94}X_{95}]_m$-Y [SEQ ID NO:17] binds to a VAKGL-binding compound and a mu opioid receptor, wherein the binding affinity of the VAKGL-binding compound is 20-fold greater for the polypeptide than the binding affinity of the VAKGL-binding compound for the mu opioid receptor.

The invention also contemplates antibodies or paratope-containing portions thereof that bind to a before-defined peptide of the formula W-$[X_1X_2X_3 \ldots X_{43}X_{44}X_{45}]_n$ValAla$X_{48}$GlyLeu$[X_{51}X_{52}X_{53} \ldots X_{94}X_{95}]_m$-Y [SEQ ID NO:17], wherein the antibodies or paratope-containing portions thereof exhibit an affinity range of about $10^7$ to about $10^{10}$ liters/mole, preferably about $10^8$ and about $10^9$ liters/mole for the peptide.

In another embodiment, the invention contemplates a method for screening a candidate VAKGL-binding compound that binds to an isolated polypeptide that includes at least the amino acid sequence Val-Ala-X-Gly-Leu (SEQ ID NO:3), the polypeptide being filamin A (FLNA) or an analog thereof having the amino acid sequence of SEQ. ID. NO:4, wherein X is an amino acid residue, comprising the steps of: (a) contacting the candidate VAKGL-binding compound with the polypeptide in an aqueous medium; (b) maintaining the contact for a time period sufficient for the candidate VAKGL-binding compound and the polypeptide to bind to each other; and (c) determining the binding of the candidate VAKGL-binding compound to the polypeptide.

In another aspect of the invention, the above method utilizes an isolated polypeptide or analog thereof containing up to 50 amino acid residues comprising a before-defined amino acid sequence W-$[X_1X_2X_3 \ldots X_{43}X_{44}X_{45}]_n$ValAla$X_{48}$GlyLeu-$[X_{51}X_{52}X_{53} \ldots X_{94}X_{95}]_m$-Y [SEQ ID NO:17].

In another embodiment, the invention contemplates a method for determining the ability of a candidate VAKGL-binding compound, other than naloxone or naltrexone, to inhibit the interaction of the mu opioid receptor with filamin A (FLNA) and thereby prevent the mu opioid receptor from coupling to Gs proteins (Gs), comprising the steps of: (a) admixing an opioid agonist and the candidate VAKGL-binding compound with mammalian cells that contain the mu opioid receptor and FLNA in their native conformations and relative orientations, the opioid agonist being present in an agonist effective amount and/or being administered in a repeated, chronic manner the VAKGL-binding compound being present in an FLNA-binding effective amount, defined herein after; and (b) determining inhibition of the interaction of the mu opioid receptor with the G protein by analysis of the presence or the absence of the Gαs subunit of Gs protein, wherein the absence of the Gαs subunit indicates inhibition of the interaction of the mu opioid receptor with the Gs protein.

In an alternate embodiment, the invention contemplates a method for determining the ability of an isolated polypeptide to interfere with candidate VAKGL-binding-compound-induced inhibition of the interaction of a mu opioid receptor with filamin A (FLNA) and thereby prevent the mu opioid receptor from coupling to Gs proteins (Gs), comprising the steps of: (a) admixing an opioid agonist and the candidate VAKGL-binding compound with mammalian cells that contain the mu opioid receptor and FLNA in their native conformations or relative orientations, the opioid agonist being present in an agonist effective amount and/or being administered in a repeated, chronic manner and the VAKGL-binding compound being present in an FLNA-binding effective amount; (b) admixing an isolated polypeptide with the mammalian cells, the polypeptide containing up to 50 amino acid residues and comprising a before-defined amino acid sequence W-$[X_1X_2X_3 \ldots X_{43}X_{44}X_{45}]_n$-ValAla$X_{48}$GlyLeu-$[X_{51}X_{52}X_{53} \ldots X_{94}X_{95}]_m$-Y [SEQ ID NO:17]; and (c) determining the presence of candidate VAKGL-binding compound-induced inhibition by analysis of the presence or the absence of the Gαs subunit, wherein the presence of inhibition indicates a failure of the polypeptide to interfere with candidate opioid antagonist-induced inhibition of the interaction of the mu opioid receptor with the Gs protein.

In another embodiment, the invention contemplates a method for inhibiting the interaction of a mu opioid receptor with a Gs protein that contains a Gαs subunit, comprising the steps of: (a) admixing an opioid agonist with mammalian cells that contain the mu opioid receptor and filamin A (FLNA) in their native conformations or relative orientations, the opioid agonist being present in an agonist effective amount and/or administered in a repeated, chronic manner; (b) admixing an FLNA-binding effective amount of an isolated polypeptide with the mammalian cells, the polypeptide containing up to 50 amino acid residues comprising a before-defined amino acid sequence W-$[X_1X_2X_3 \ldots X_{43}X_{44}X_{45}]_n$-ValAla$X_{48}$GlyLeu$[X_{51}X_{52}X_{53} \ldots X_{94}X_{95}]_m$-Y [SEQ ID NO:17]; and (c) determining the inhibition by analysis of the presence or the absence of the Gαs subunit, wherein the absence of the Gαs subunit indicates inhibition of the interaction of the mu opioid receptor with the Gs protein.

In another aspect of the invention, in any of the three method embodiments presented above related to inhibiting, or the interference of inhibiting, the interaction of the mu-opioid receptor with a Gs protein further comprises the steps of: (d) measuring the levels of cAMP production (Gβγ adenylyl cyclase interaction-downstream regulation) and (e) measuring the levels/presence of $S^{133}$ phosphorylation (CREB activation-downstream regulation). The additional steps of (d) and (e), as well as alternate downstream effects apparent to one of ordinary skill to effectively monitor the changes in the downstream effects due to the alterations in the interaction between the mu opioid receptor with a Gs protein elicited from either a candidate VAKGL-binding compound or a polypeptide of the invention.

In another aspect of the invention, determination of inhibition of the interaction of a mu-opioid receptor with a G protein comprises monitoring any cellular signals known to one of ordinary skill in the art as indicative of inhibition of MOR-Gs coupling; inhibition of adenylyl cyclase types II and IV with the Gβγ subunits of the Gs protein and levels of cAMP production, or inhibition of CREB activation by phosphorylation of CREB $S^{133}$, and any other processes known to one of ordinary skill in the art to be associated with opioid agonist and VAKGL-binding compound admixtures with mammalian cells.

In one aspect, the analysis of Gs protein coupling by the mu opioid receptor and downstream effects elicited by admixing mammalian cells with a before-defined peptide can be conducted by any one or more of several methods such as for example Western blot analysis, densitometric quantification of Western blots, and detection of labeled candidate opioid antagonist binding.

An additional aspect of the invention is a method for selecting a compound for VAKGL-binding activity that preferably also possesses mu opioid receptor agonist activity from candidate compounds. That method comprises the steps of: a)

determining the aromatic/hydrophobic and hydrogen bond acceptor functions and the distances there between of a candidate compound; and b) selecting a compound that exhibits at least three of the pharmacophores shown in FIGS. 12-27. A selected VAKGL-binding compound can bind to the VAKGL-binding site of filamin A alone, but will preferably also be an agonist at the mu-opioid receptor. A selected compound preferably exhibits at least six of the sixteen pharmacophores, more preferably at least nine of those pharmacophores, and most preferably at least twelve of the sixteen pharmacophores.

A contemplated method contacts one or more of the VAKGL-binding compound and/or a contemplated polypeptide (active component) with mammalian cells. That contacting (admixture) can occur in vitro or in vivo in a mammalian subject. The contacting is generally repeated several times, and typically takes place as a result of the VAKGL-binding compound and/or a contemplated polypeptide being dissolved or dispersed in a physiologically acceptable diluent, forming a pharmaceutical composition, as is well known in the pharmaceutical arts.

A contemplated pharmaceutical composition can then be administered orally, parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal whose cells are contacted can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where in vitro mammalian cell contact is contemplated, a CNS tissue culture of cells from an illustrative mammal is often utilized, as is illustrated hereinafter. In addition, a non-CNS tissue preparation that contains opioid receptors such as guinea pig ileumcan also be used.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, in vials or ampules.

I. Chronic Morphine-Induced MOR-Gs Coupling Results from Interactions Between FLNA and MOR and is Prevented by an Opioid Antagonist, NLX FIG. 1 illustrates the identification of NLX-binding protein in MOR immunoprecipitates. A protein with molecular weight at approximately 300-KDa was noted in Gαi/o immunoprecipitates in an amount that closely paralleled the amount of MORs in the immunoprecipitates. A battery of antibodies against various cytoskeletal proteins was used to identify this protein that co-immunoprecipitated with MORs and their associated G proteins from striatal tissue of rats treated chronically with vehicle, morphine, ultra-low-dose NLX or morphine+ultra-low-dose NLX.

Antibodies to FLNA exclusively stained this novel protein robustly, whereas antibodies to other cytoskeletal proteins including $MAP_{1B}$ and yaotio were without detection (FIGS. 1E-1H). Thus, preliminarily suggesting that FLNA is a protein target through which ultra-low-dose NLX blocks the chronic morphine-induced switch from normal MOR-Gi/o coupling to MOR-Gs coupling. Additionally, in a two-tiered co-immunoprecipitation using anti-Gα followed by anti-MOR antibodies, it was demonstrated that FLNA associates with Go-coupled MOR and not with Gs-coupled MOR (FIG. 1A-FIG. 1D). Blots stripped and re-probed with antibodies to $MAP_{1B}$ and yaotio illustrate the absence of these cytoskeletal proteins in these immunoprecipitates (FIG. 1E-FIG. 1H).

Figure 2:
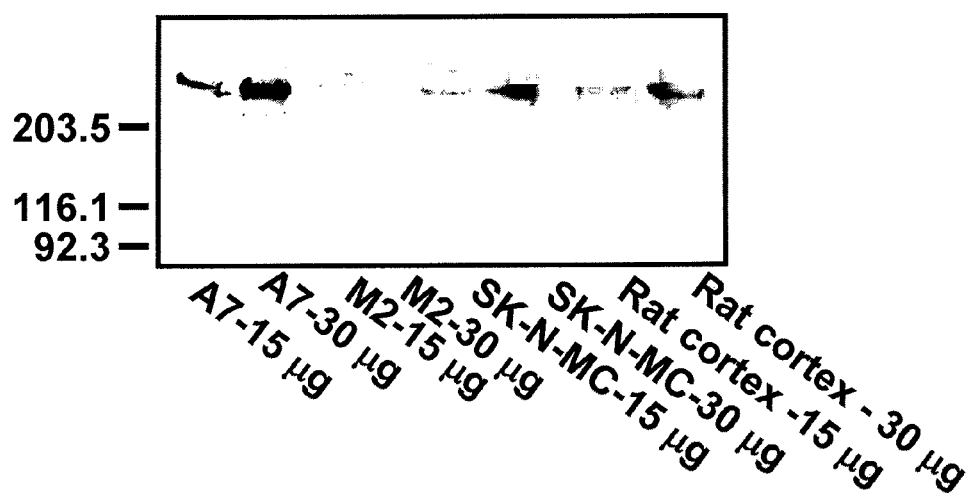
FIG. 2 illustrates FLNA expression in MOR-deficient cell types, A7 and M2.
Figure 3A:
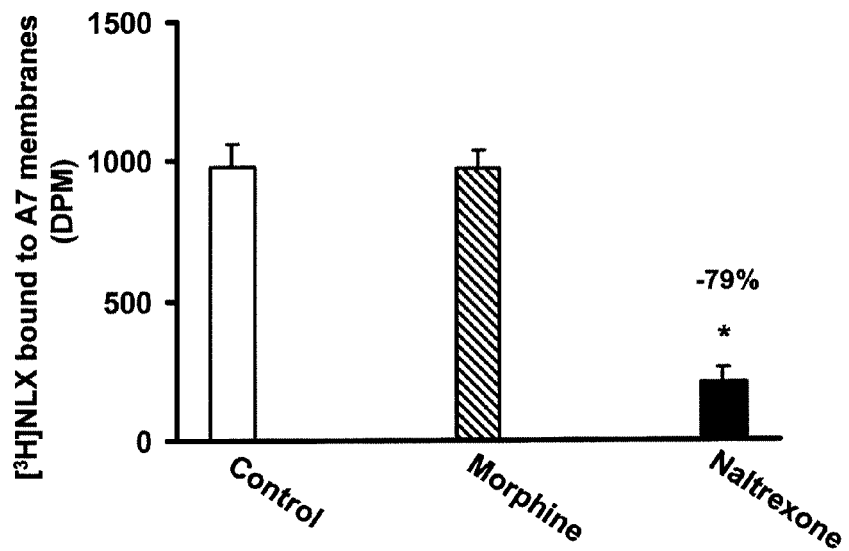
FIG. 3, in three parts, 3A demonstrates confirmation of a novel binding site for NLX on FLNA by detection of [$^3$H] NLX binding in A7 cell membranes after binding site occupancy competition by morphine or naltrexone.
FIG. 3B confirms the absence of MOR in the A7 cell membranes due to negligible [$^3$H]DAMGO binding.
FIG. 3C demonstrates lack of [$^3$H]NLX binding in the FLNA-deficient M2 cells.
Figure 3B:
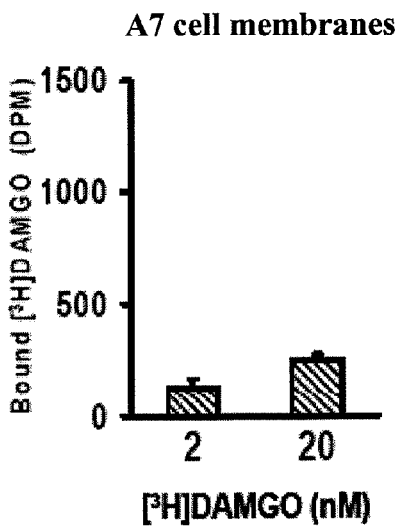
Figure 3C:
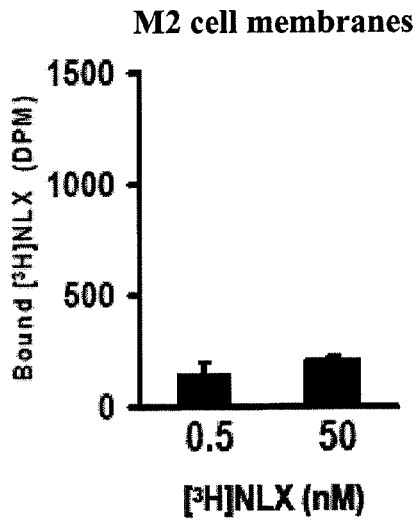

FIG. 2 and FIG. 3 illustrate further validation of NLX and FLNA binding. Binding of [$^3$H]NLX to membranes prepared from the human melanoma cell line M2 that lacks filamin and to the M2 subclone A7 stably transfected with human FLNA cDNA was analyzed. Confirmation of FLNA expression in A7 cells and absence in M2 cells by Western blotting using a specific anti-FLNA antibody is shown in FIG. 2. FLNA was also detected in the human neuroblastoma SK-N-MC cell line and in rat cortical synaptic membranes (FIG. 2). A7 cells (and presumably their M2 parent line) do not express MORs due to negligible [$^3$H]DAMGO binding (FIG. 3b). Unlike the FLNA-expressing A7 cells, the filamin-deficient M2 cells do not express molecules that bind [$^3$H]NLX (FIG. 3c)

Importantly, [$^3$H]NLX bound to A7 membranes and this binding was robustly displaced by NTX but not by morphine, illustrating that NLX and NTX bind to a novel site distinct from their binding site on MORs (FIG. 3a).

A high-affinity binding site for NLX has been identified in the carboxyl-terminal region of the scaffolding protein FLNA. These data further elucidate the mechanism of action of certain ultra-low-dose opioid antagonists in enhancing opioid analgesia and preventing opioid tolerance and dependence by preventing a G protein coupling switch by MOR (Wang et al., 2005 *Neuroscience* 135:247-261).

Naloxone binds immunopurified FLNA with a binding affinity of about 43 pM, i.e. 20-fold higher than the NLX binding affinity for MOR. This is the first demonstration of picomolar binding by a psychoactive compound that is not to a cell surface receptor.

Figure 4:
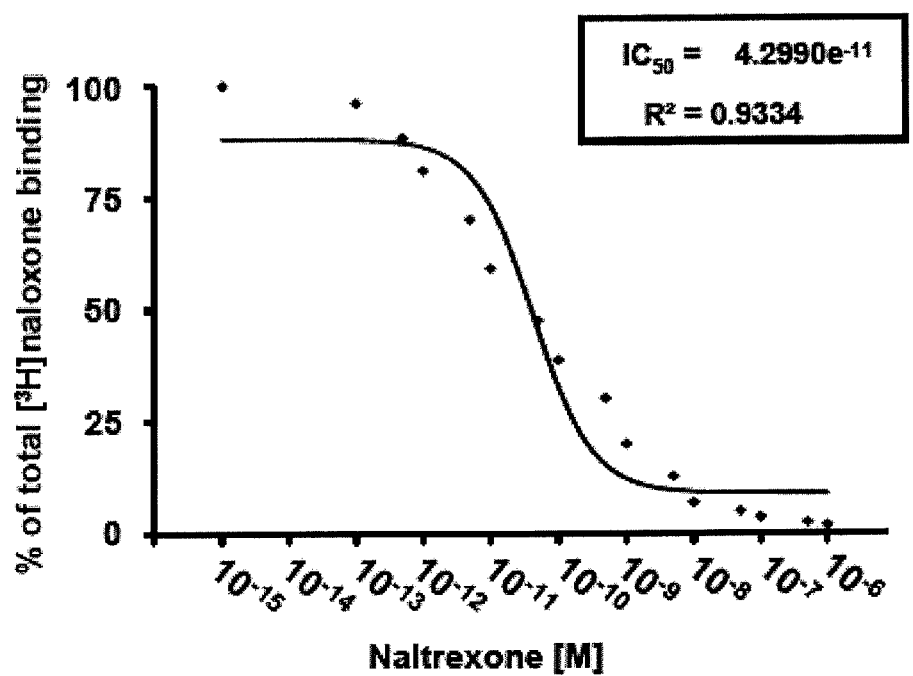
FIG. 4 illustrates a competition (displacement) curve for the inhibition of [$^3$H]NLX binding by naltrexone to membranes from FLNA-expressing A7 cells and the resulting $IC_{50}$ of 43 picomolar.

A competition (displacement) curve for the inhibition of [$^3$H]NLX binding by naltrexone to membranes from FLNA-expressing A7 cells was generated. A nonlinear curve-fit analysis was performed using competition equation that assumed one saturable site for naltrexone curve comprising of 16 concentrations ranging from 0.2 µM to 1 µM. Six studies each using a different set of A7 cells were included in the analysis, results are shown in FIG. 4.

Data using organotypic striatal slice cultures suggest that a binding site on FLNA is responsible for ultra-low-dose NLX's prevention of the MOR-Gs coupling that has been shown to result from chronic opioid administration (Wang et al., 2005 *Neuroscience* 135:247-261; Chakrabarti et al., 2005 *Mol Brain Res* 135:217-224). Accordingly, the multiple beneficial effects of ultra-low-dose opioid antagonists to enhance opioid analgesia, to reduce opioid tolerance and dependence (Crain et al., 1995 *Proc Natl Acad Sci USA* 92:10540-10544; Powell et al. 2002 *J Pharmacol Exp Ther* 300:588-596), and to attenuate the addictive properties of opioids (Olmstead et al., 2005 *Psychopharmacology* 181:576-581; Leri et al., 2005 *Pharmacol Biochem Behav* 82:252-262) can all be mediated by this high-affinity binding to FLNA.

The presence of FLNA in MOR signalplex in native brain tissues demonstrated by co-immunoprecipitation, agrees with previous data using yeast-two hybrid and co-transfection methods (Onoprishvili et al., 2003 *Mol Pharmacol* 64:1092-1100). The fact that NLX prevents MOR-Gs coupling at concentrations well below its affinity for MOR hinted that NLX can interact with a component of the MOR signalplex such as FLNA to prevent MOR's tolerance-driven Gi/o-to-Gs coupling switch. This hypothesis is supported by significant binding of [$^3$H]NLX in MOR-deficient, FLNA-expressing A7 cells but not in M2 cells lacking FLNA, and by [$^3$H]NLX binding to immunopurified FLNA. The absence of MOR in these cells clarified a novel target for NLX and NTX due to the fact that NTX but not morphine displaced the [$^3$H]NLX.

Figure 5A:
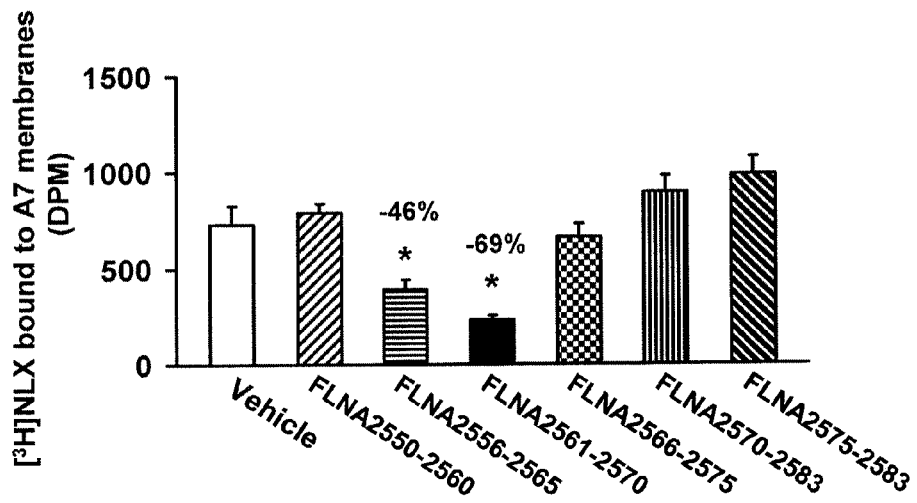
FIG. 5 identifies a NLX binding site on FLNA using overlapping FLNA C-terminal peptide fragments (FIG. 5A) and full length FLNA purified from A7 cells (FIG. 5B) as NLX binding targets by detection of [$^3$H]NLX binding.
Figure 5B:
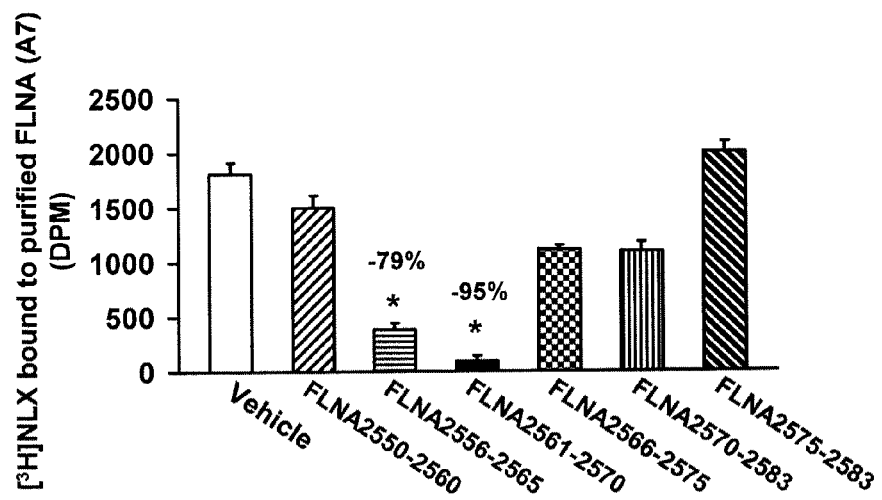
Figure 6:
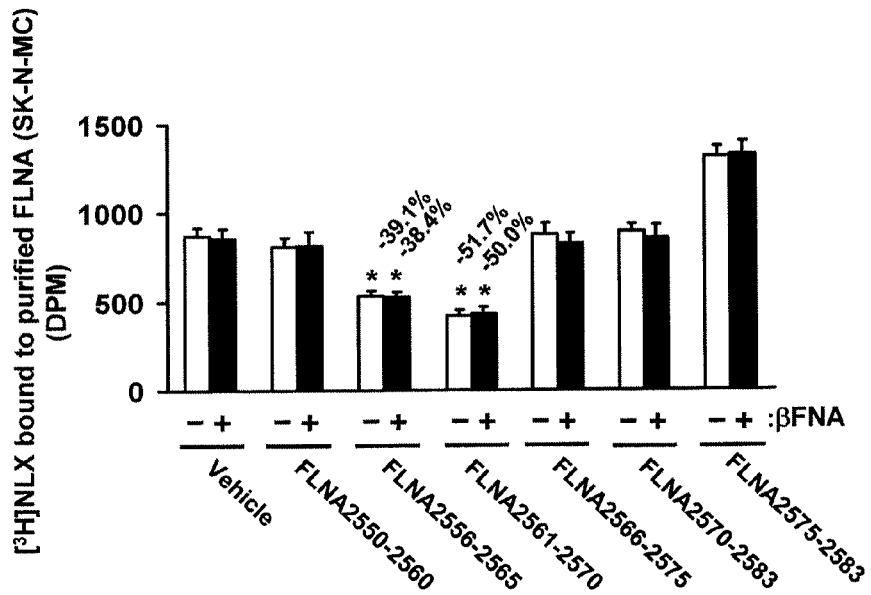
FIG. 6 confirms NLX binds to FLNA, not MOR, by detection of [$^3$H]NLX binding to FLNA purified from SK-N-MC cells in the absence and presence of the irreversible MOR antagonist, βFNA.

II. Identification of the Pentapeptide (VAKGL-Containing) Binding Site Along FLNA to which Opioid Antagonists (NLX/NTX) Bind to Prevent Chronic Morphine-Induced MOR-Gs Coupling To deduce the precise binding domain within FLNA where NLX binds, several overlapping peptide sequences derived from the carboxy-terminus where FLNA intersects with synaptic membranes were used to absorb [$^3$H]NLX. Both FLNA$_{2556-2565}$ and FLNA$_{2561-2570}$ markedly attenuated [$^3$H] NLX binding to A7 cell membranes and to purified human FLNA (FIG. 5). This result was confirmed using FLNA purified from FLNA- and MOR-expressing SK-N-MC cells. At 500 pM concentration, [$^3$H]NLX binds to immunoaffinity-purified FLNA in the presence or absence of irreversible MOR antagonist, β-FNA (FIG. 6). These data together suggest that NLX binds with high affinity to FLNA with the binding site located at FLNA$_{2561-2565}$.

The critical NLX-interacting domain was determined by using several overlapping peptide fragments encoding the c-terminus of FLNA to compete for [$^3$H]NLX binding. FLNA$_{2556-2565}$ and FLNA$_{2561-2570}$ both markedly reduced [$^3$H]NLX binding to A7 membranes or to FLNA proteins purified from A7 or SK-N-MC cells, indicating that FLNA$_{2561-2565}$, within the 24$^{th}$ repeat, is the NLX-binding site on FLNA. The binding site (FLNA$_{2561-2565}$) was confirmed by showing NLX binds FLNA tightly with critical involvement of a pentapeptide VAKGL-containing binding site along FLNA, FLNA$_{2561-2565}$, a 5-amino acid residue segment that is likely intracellular but near its c-terminal transmembrane domain.

Figure 7:
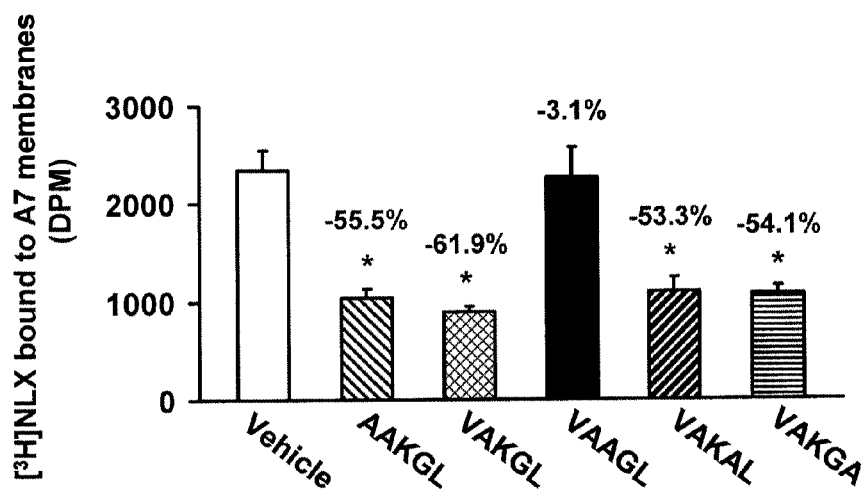
FIG. 7 identifies a critical amino acid residue in the NLX binding site of FLNA by detection of [$^3$H]NLX binding to FLNA in A7 cell membranes in the presence of various alanine scanning peptides.

III. An Essential Lysine Residue (Lys$_{2663}$) Resides within the VAKGL-Containing Binding Site To confirm that FLNA$_{2561-2565}$ binds NLX and to deduce the critical amino acid residue(s) within the NLX interacting FLNA$_{2561-2565}$ region, four alterations of FLNA$_{2561-2565}$ were prepared, each with 1 amino acid residue replaced by alanine (alanine scan). Using these alanine-replaced pentapeptides to compete with [$^3$H]NLX binding to FLNA in A7 cell membranes, the data show that the lysine residue located on FLNA$_{2663}$ is critical to the NLX-FLNA interaction. Although alanine substitutions at the first, fourth and fifth amino acid residues only mildly attenuated the FLNA$_{2561-2565}$ displacement of [$^3$H]NLX binding from A7 membranes, the alanine substitution of the lysine completely prevented it (FIG. 7).

An alanine scan of this pentapeptide revealed that the lysine at FLNA$_{2563}$ is critical for binding. Finally, the functional significance of this high-affinity NLX-FLNA interaction was demonstrated in organotypic striatal slice cultures. By competing with full-length FLNA in the tissues for NLX binding, peptides containing FLNA$_{2561-2565}$ were able to block NLX's prevention of both the chronic opioid-induced G protein coupling switch by MOR and the downstream effects on cAMP accumulation. Collectively, these data provide evidence that ultra-low-dose NLX enhances opioid analgesia and blocks tolerance and dependence by binding to MOR-associated FLNA at approximately FLNA$_{2561-2565}$.

Figure 8A:
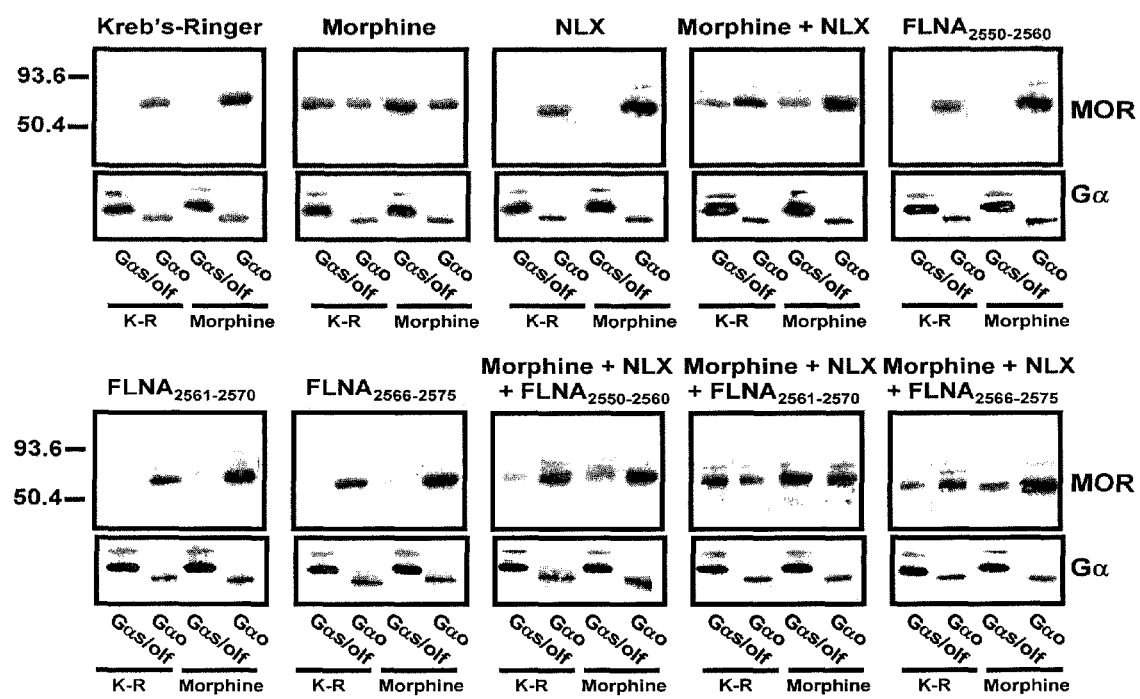
FIG. 8, in twenty parts, demonstrates the ability of the peptide $FLNA_{2561-2570}$ to interfere with ultra-low-dose NLX-facilitated inhibition of morphine-induced MOR-Gs coupling in organotypic striatal slice cultures by Western blot (FIG. 8A-FIG. 8J) and densitometric quantitation of those blots (FIG. 8K-8T).
Figure 8B:
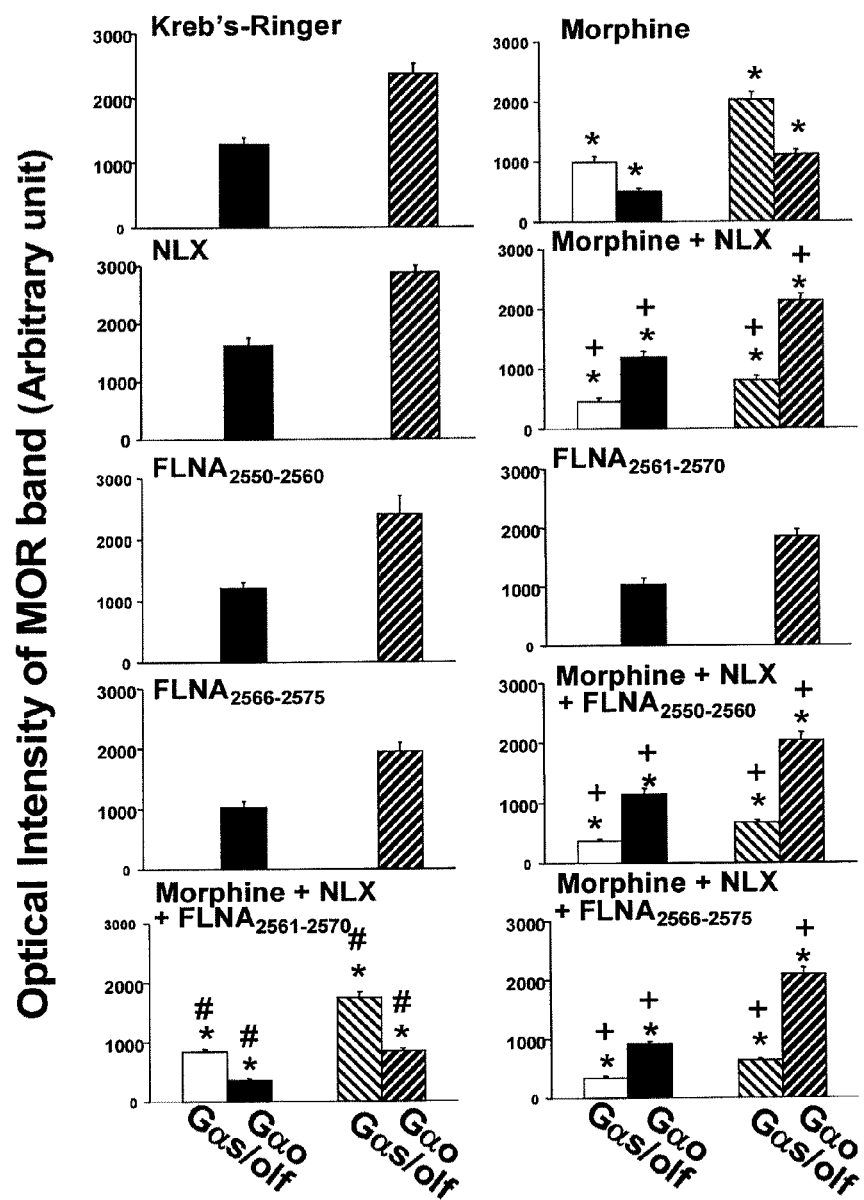

IV. Chronic Morphine Induced MOR-Gs Coupling and cAMP Accumulation is Prevented by Administration of an Ultra-Low-Dose Opioid Antagonist (NLX/NTX) and this Protective Effect is Blocked by a VAKGL-Containing Peptide that Prevents NLX/NTX Binding to Full-Length FLNA in the Tissues To confirm that NLX binding to FLNA prevents the chronic morphine-induced Gi/o to Gs coupling switch, organotypic rat brain striatal slice cultures were utilized. It has previously been shown that in vivo chronic morphine induced a switch to MOR-Gs coupling in rat striatum, periaqueductal gray and dorsal spinal cord from Gi or Go coupling in these latter two regions but from an exclusive Go coupling in striatum (Crain et al., 2001 *Brain Res* 888:75-82). To mimic the in vivo chronic morphine treatment and resulting opioid tolerance in that study, rat striatal slices were treated twice daily for 1 hour with 100 µM morphine in serum-free culture medium. This morphine treatment induced a robust Go-to-Gs coupling switch, similar to that previously observed following in vivo chronic morphine (FIG. 8).

Figure 9:
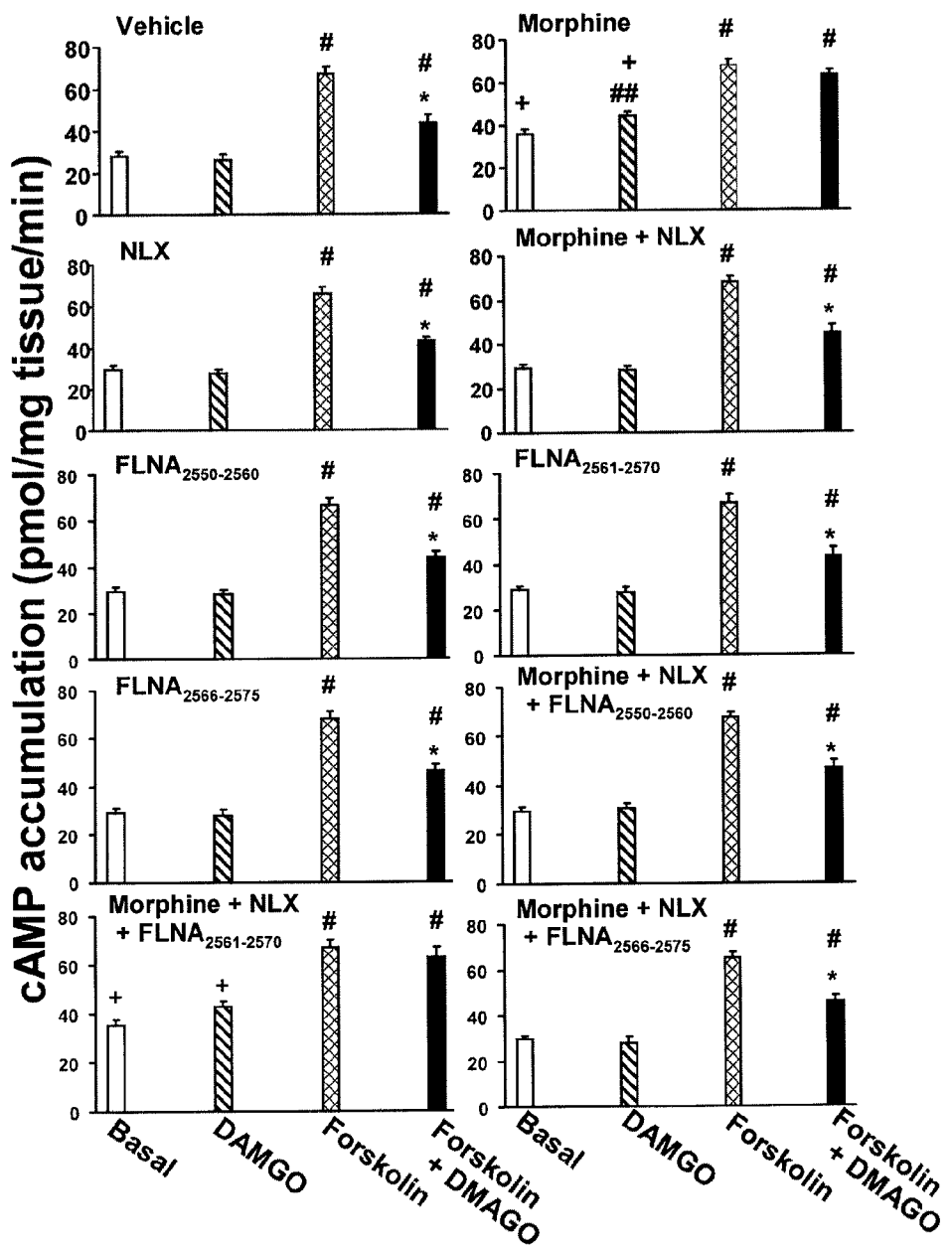
FIG. 9, in ten parts (9A-9J), demonstrates the ability of the purified peptide $FLNA_{2561-2570}$ to prevent inhibition of cAMP accumulation by ultra-low-dose NLX co-administration by measuring the levels of cAMP produced in organotypic striatal slice cultures in the presence of DAMGO and/or Forskolin.
Figure 10A:
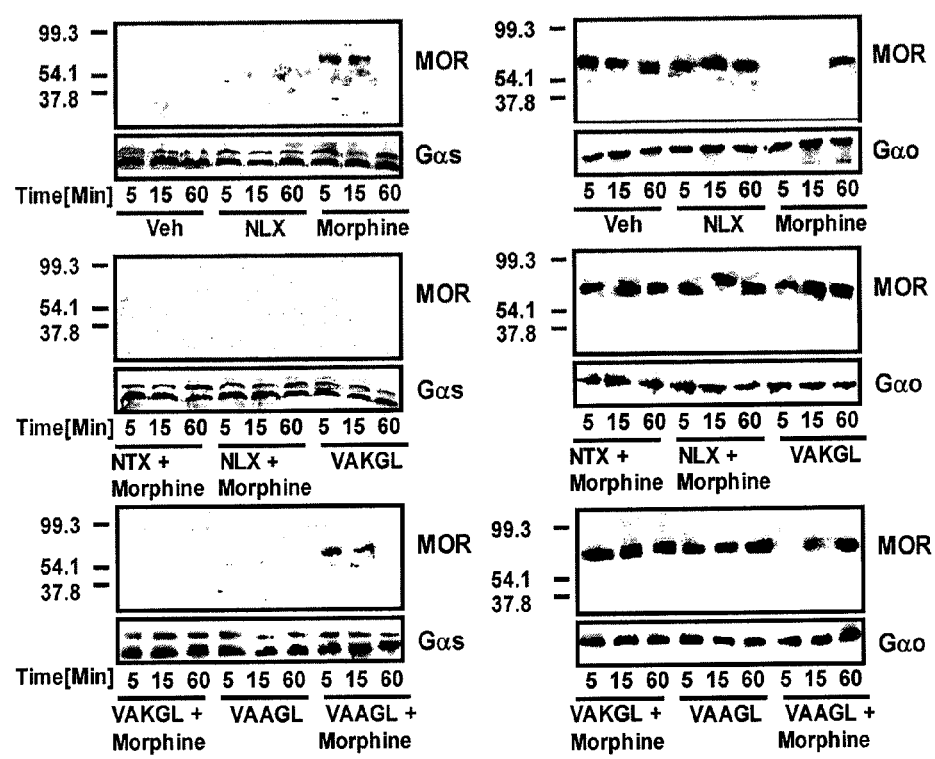
FIG. 10, in twelve parts (10A-10L) represents inhibition of the acute morphine-induced Go-to-Gs coupling switch in organotypic striatal slice cultures by $FLNA_{2561-2565}$ (or VAKGL (SEQ ID NO:14)), ultra-low-dose NLX, and ultra-low-dose NTX, by Western blot (FIG. 10A-FIG. 10F) and densitometric quantitation of these blots (FIG. 10G-FIG. 10L).
Figure 10B:
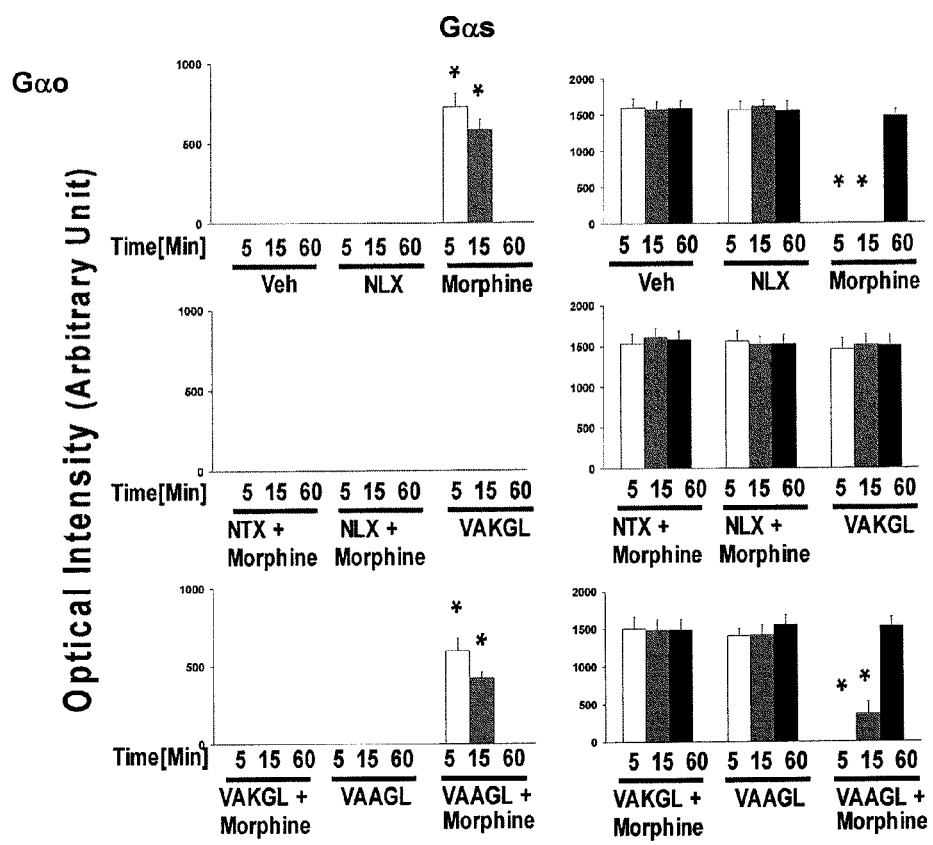
Figure 11A:
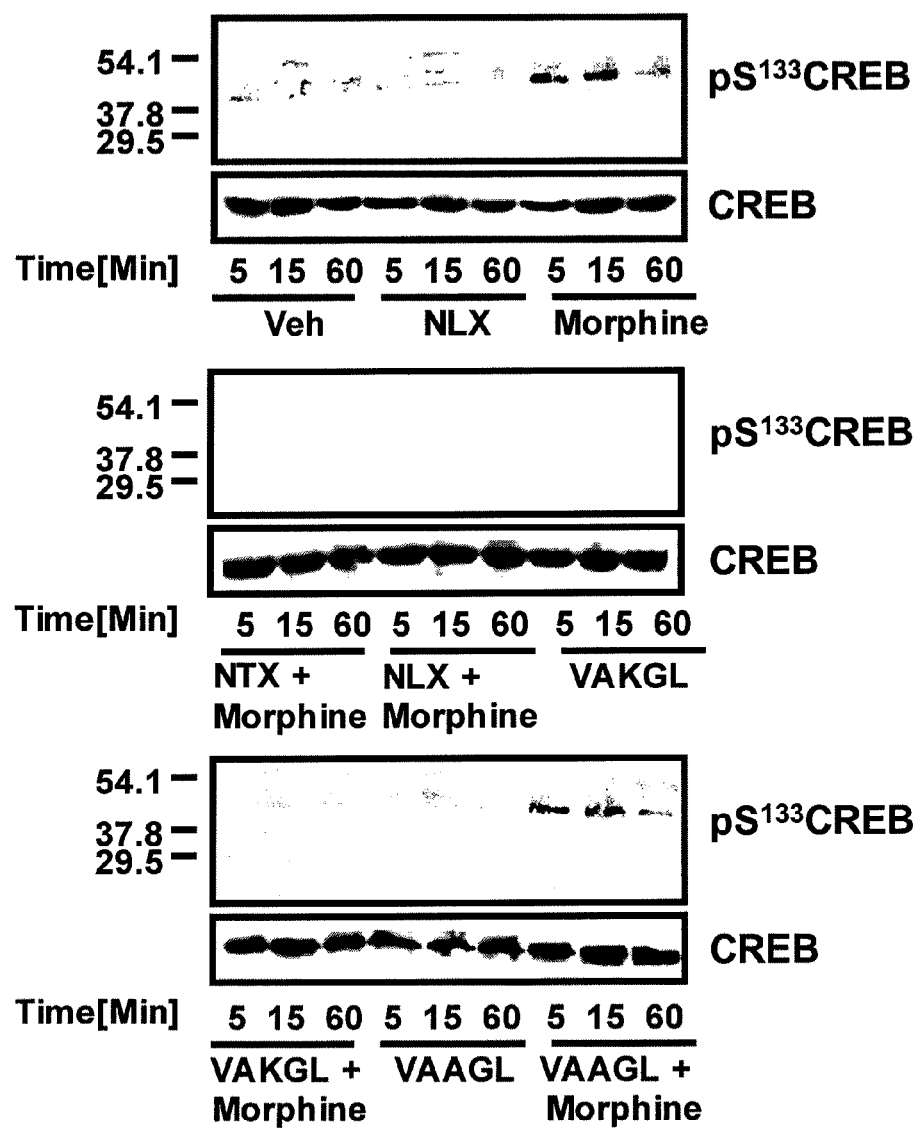
FIG. 11, in six parts, represents inhibition of the acute high-dose morphine-induced activation of CREB (CREB $S^{133}$ phosphorylation) in organotypic striatal slice cultures by $FLNA_{2561-2565}$ (or VAKGL (SEQ ID NO:14)), ultra-low-dose NLX and ultra-low-dose NTX by Western blot analysis (FIG. 11A-FIG. 11C) and densitometric quantitation of these blots (FIG. 11D-11F).
Figure 11B:
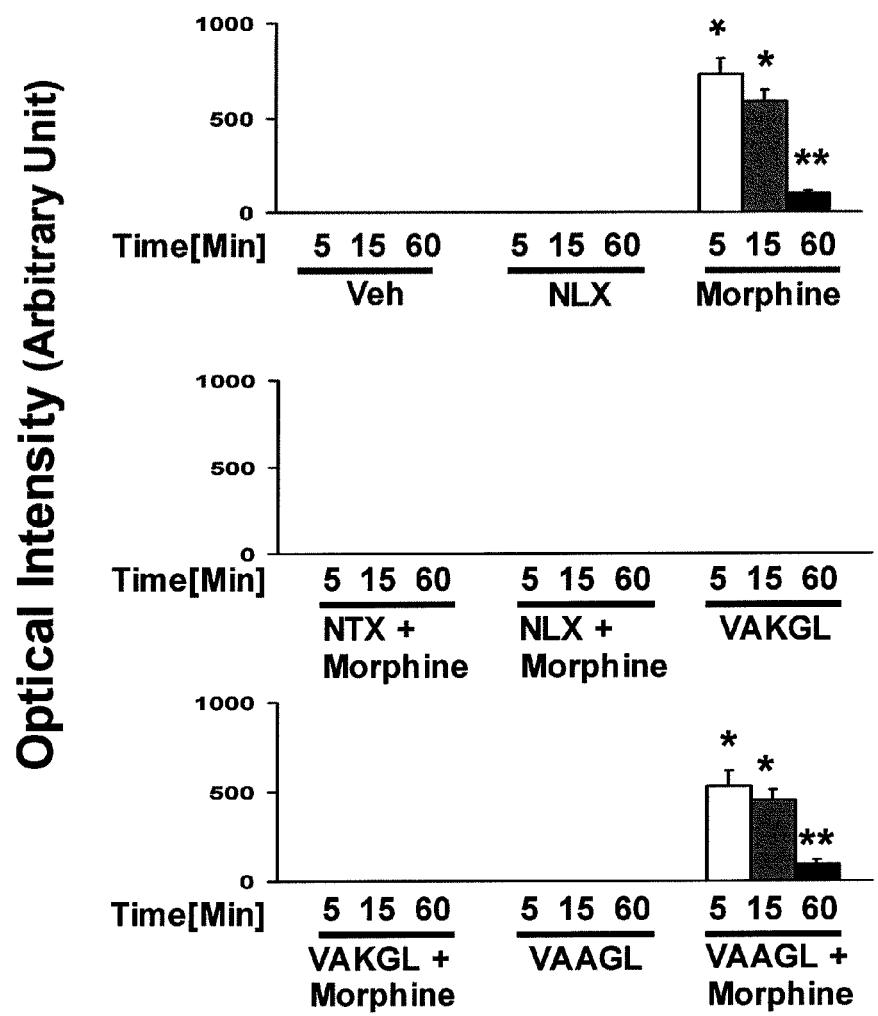
Figure 12:
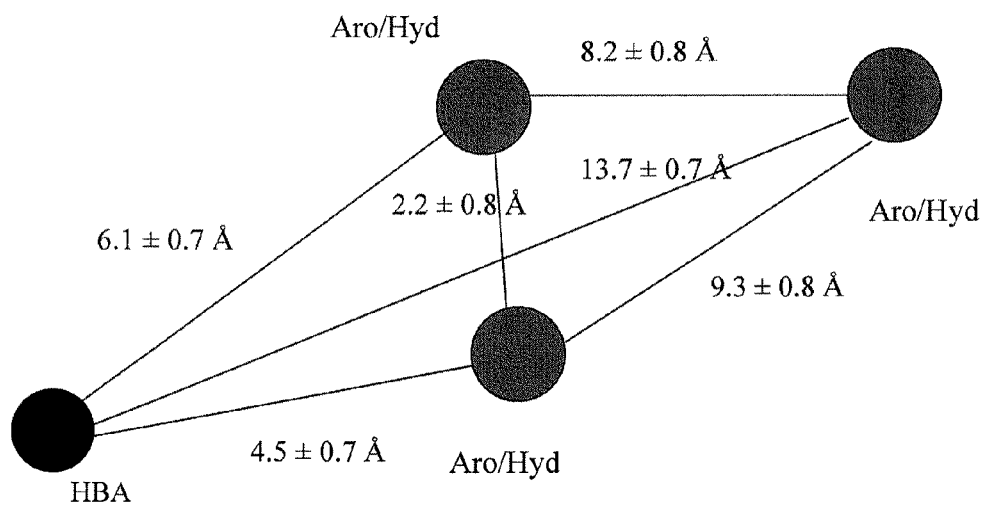
FIGS. 12-27 represent schematic pharmacophores showing relative locations of chemical features such as a hydrogen bond acceptor (HBA) and an aromatic/hydrophobe (ARO/HYD) center, and the intramolecular distances therebetween in Ångstroms.
Figure 13:
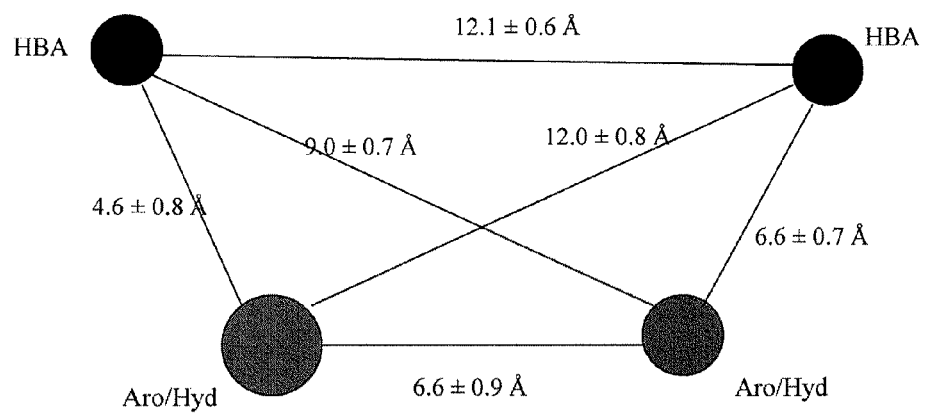
Figure 14:
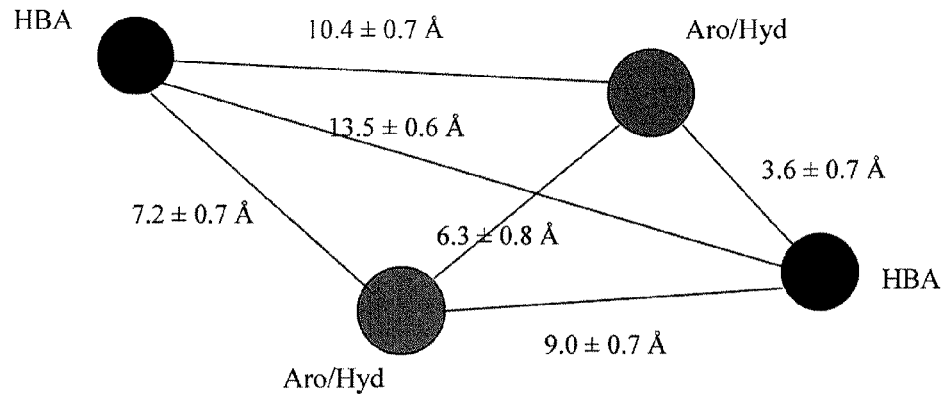
Figure 15:
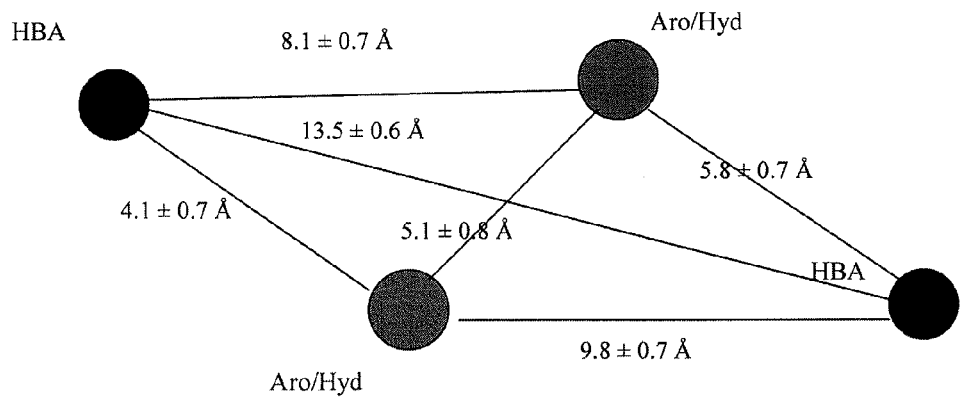
Figure 16:
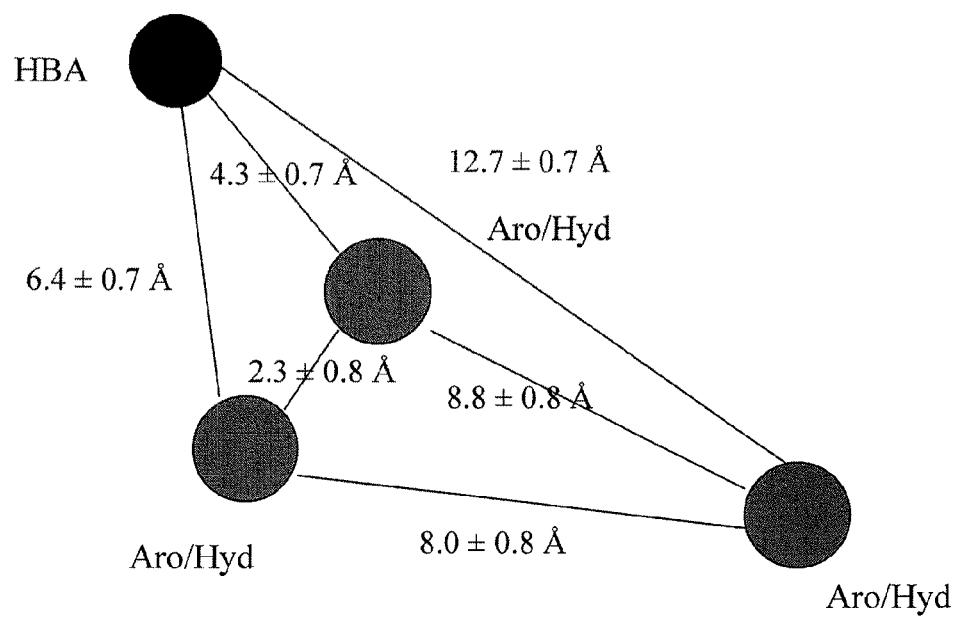
Figure 17:
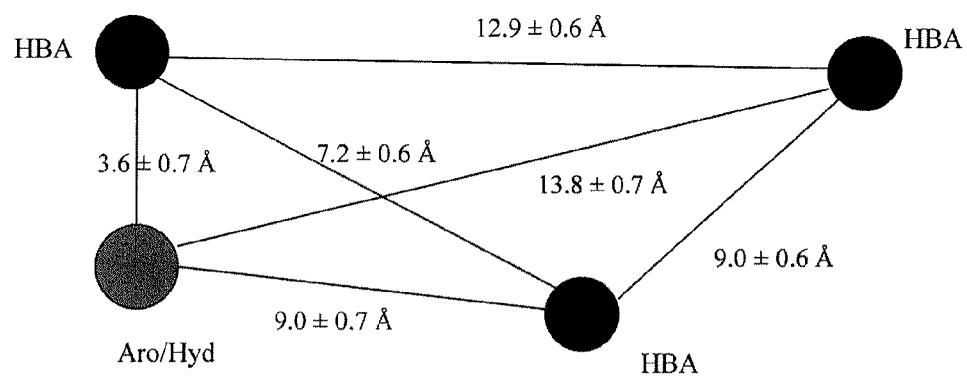
Figure 18:
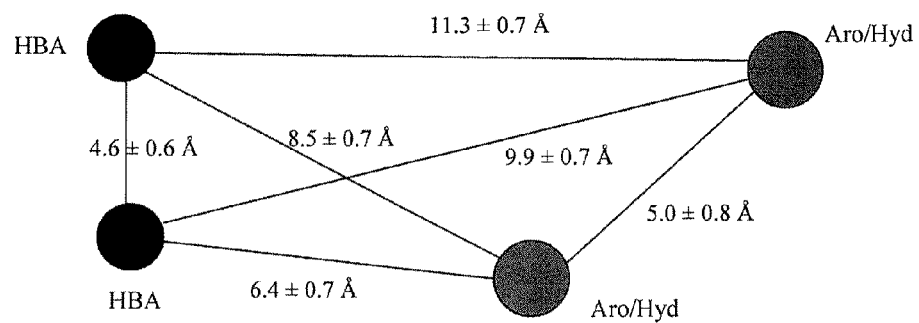
Figure 19:
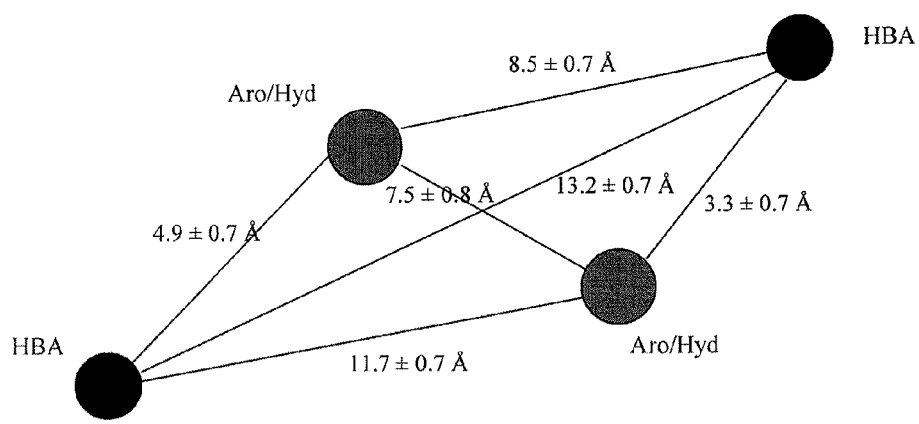
Figure 20:
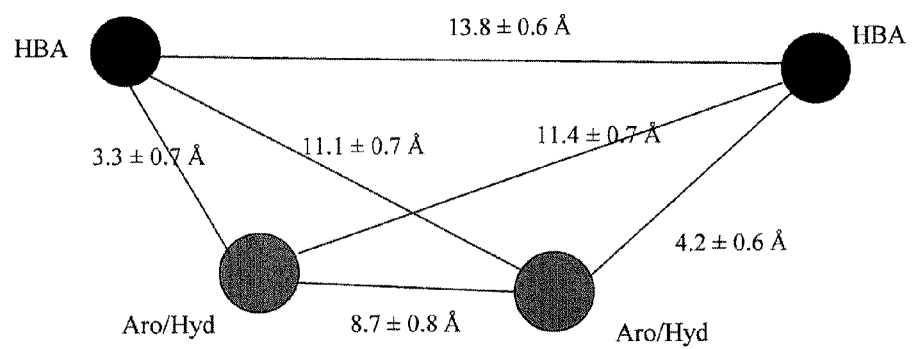
Figure 21:
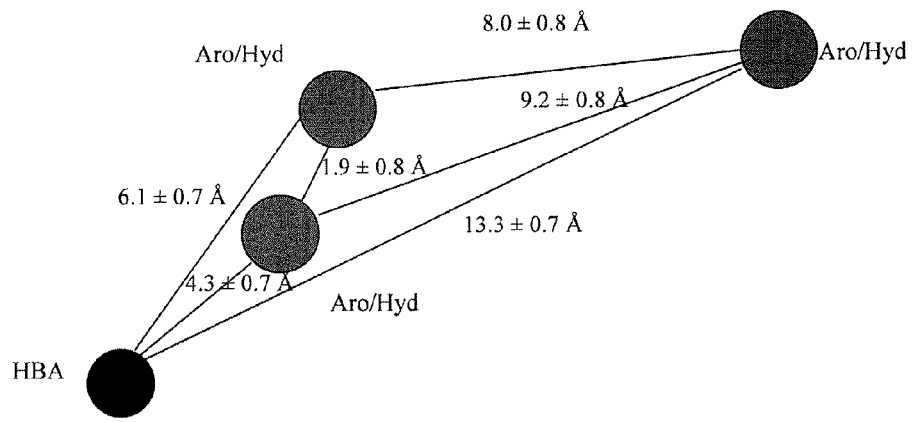
Figure 22:
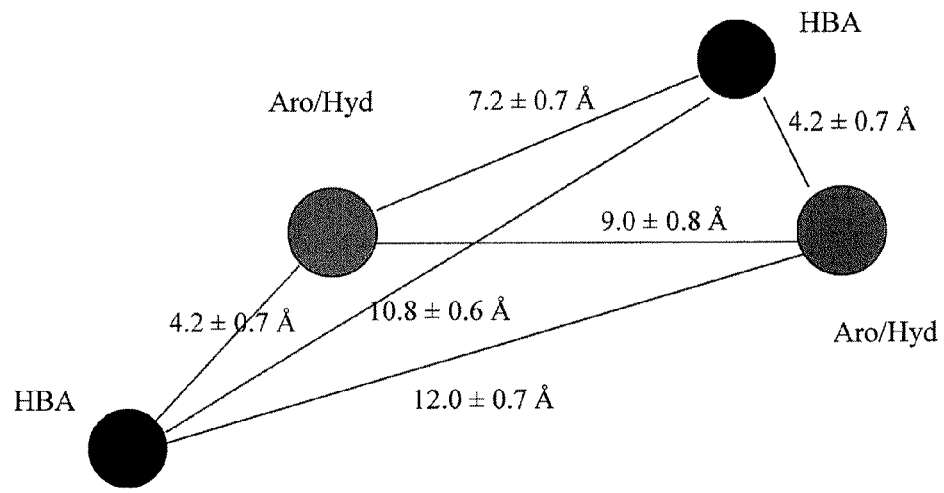
Figure 23:
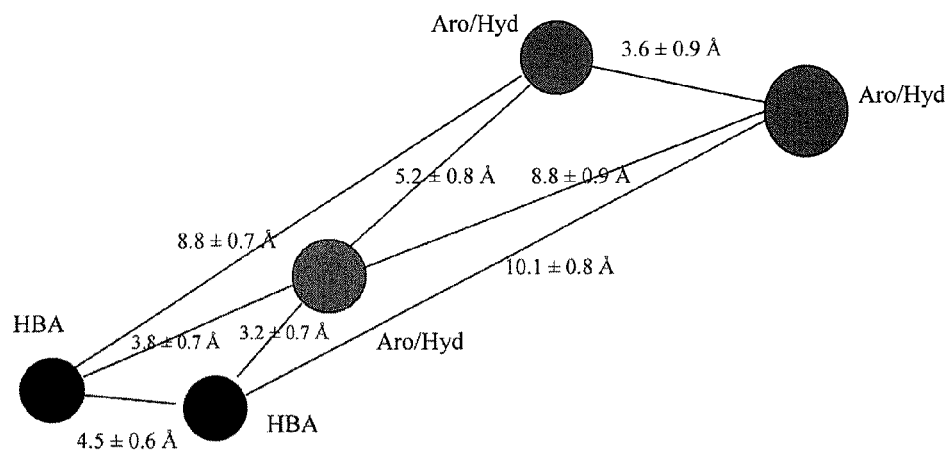
Figure 24:
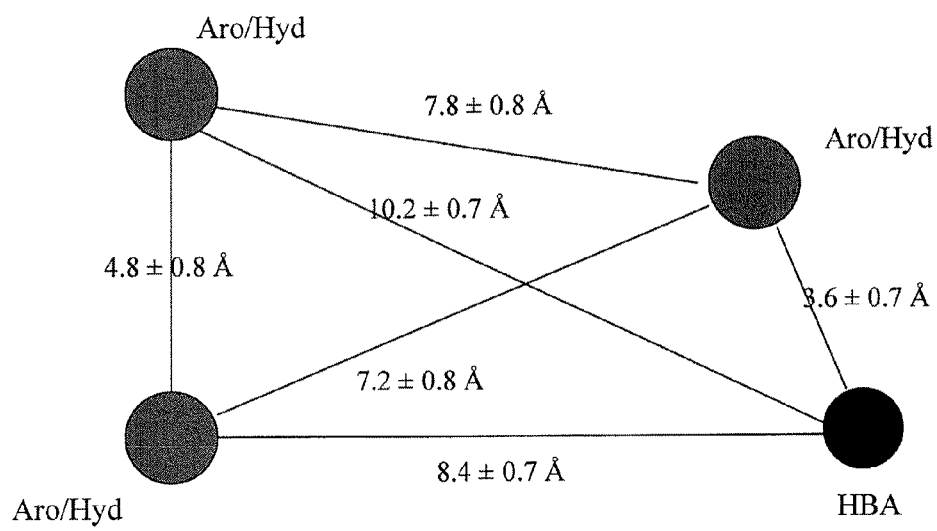
Figure 25:
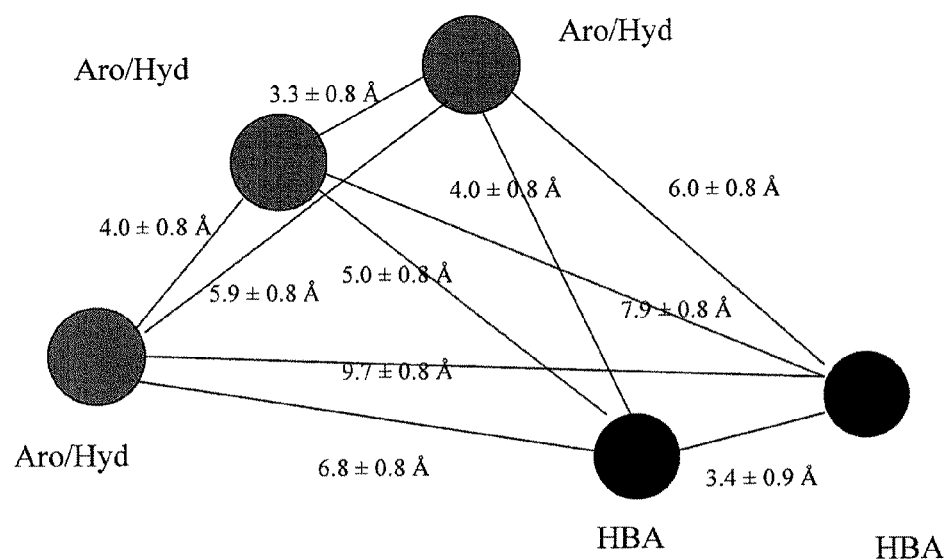
Figure 26:
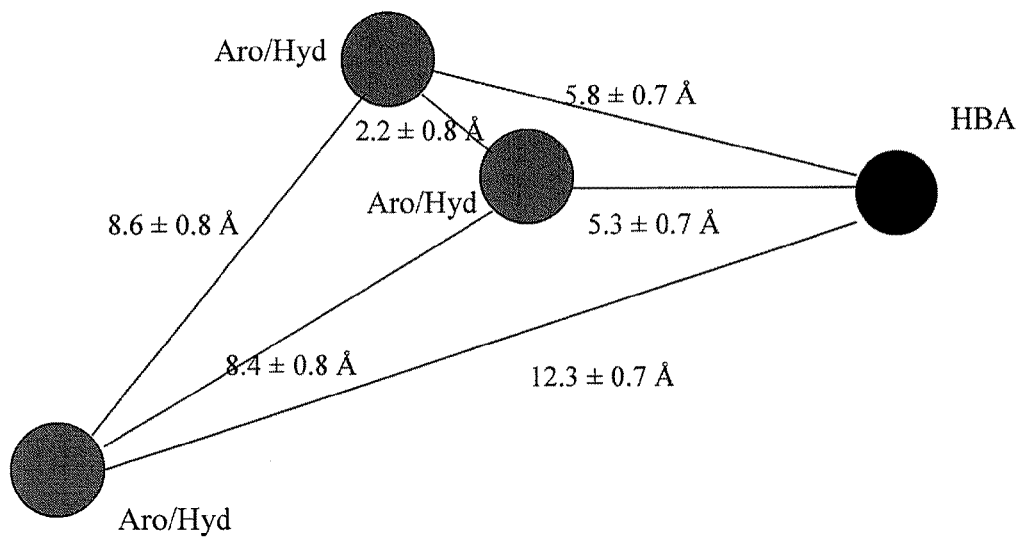
Figure 27:
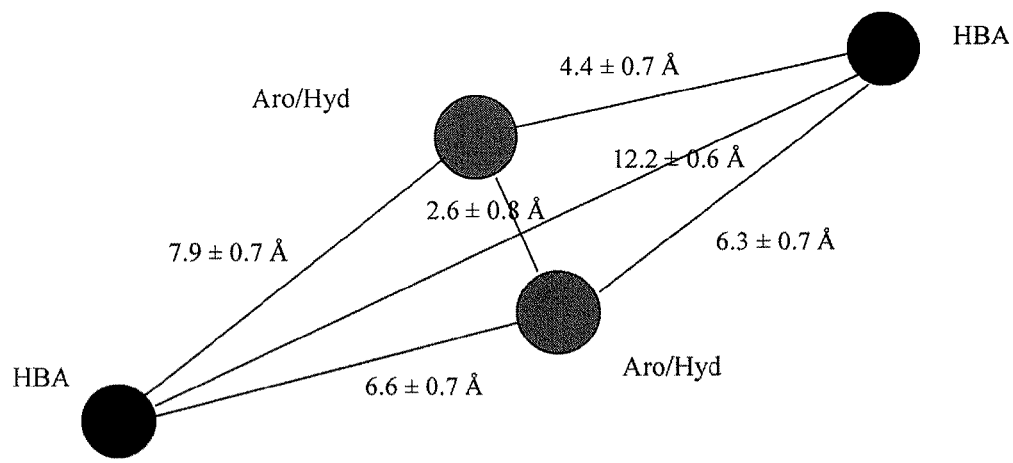

Morphine treatment also attenuated the DAMGO-mediated reduction in cAMP accumulation, an effect consistent with the G protein coupling switch (FIG. 9). Ultra-low-dose NLX (10 pM) blocked both the chronic morphine-induced Go-to-Gs coupling switch and the attenuation of the DAMGO-induced reduction in cAMP production (FIGS. 8 and 9).

The addition of FLNA$_{2561-2570}$ but not FLNA$_{2550-2560}$ or FLNA$_{2566-2575}$ abolished the NLX-mediated prevention of these cellular indices of morphine tolerance. These data together suggest that ultra-low-dose NLX prevents analgesic tolerance in response to chronic morphine by binding to a specific region of FLNA.

The detection of FLNA in immunoprecipitates containing Go-coupled MOR and not Gs-coupled MOR appears counterintuitive due to NLX's prevention of MOR-Gs coupling via tight binding to FLNA.

It is thought that repeated MOR stimulation can force a particular conformation of the MOR-FLNA complex that weakens the entire signalplex. MOR subsequently releases from both its native G protein and from FLNA itself leading to association with Gs without FLNA in the complex.

By binding to FLNA, NLX blocks this particular MOR-FLNA interaction and stabilizes the MOR-FLNA-G protein complexes, thereby reducing the morphine-induced release of MORs and their subsequent coupling with Gs in response to receptor stimulation. Although FLNA was observed in MOR signalplexes containing Go proteins, the prior data in co-transfected cells indicates that FLNA is not required for the native coupling state of MOR; in fact, its absence actually enhances MOR function (Onoprishvili et al., 2003 *Mol Pharmacol* 64:1092-1100).

The above study by Onoprishvili et al., shows interactions between FLNA and the c-terminal of MOR and proposed a role for FLNA in receptor regulation and trafficking. Those workers reported that MOR functioned normally in cells lacking FLNA, but that the agonist DAMGO was unable to desensitize MOR, as measured by the decreased ability of DAMGO to inhibit forskolin-mediated cAMP accumulation following prolonged DAMGO exposure.

Slice culture data of the present invention confirm this and show that ultra-low-dose NLX, by binding to FLNA, prevents this morphine-induced desensitization measure, as well as the upstream MOR-Gs coupling that was previously shown to underlie tolerance and dependence in vivo (Wang et al., 2005 *Neuroscience* 135:247-261).

Rather than desensitization, Onoprishvili et al. actually noted enhanced inhibition by DAMGO of cAMP accumulation in cells lacking FLNA (Onoprishvili et al., 2003 *Mol Pharmacol* 64:1092-1100), a finding that also agrees with the idea that in signaling complexes that do not contain FLNA, MOR does not release from its Gi/o protein to interact with Gs. This increased Gi/o recruitment leading to heightened DAMGO-induced cAMP inhibition also concurs nicely with the increased Gi/o coupling previously observed in spinal cord of animals treated with morphine+ultra-low-dose NLX (Wang et al., 2005 *Neuroscience* 135:247-261), as well as with the enhanced analgesia that follows these co-treatments.

The "paradoxical" enhancement of opioid analgesia and reduction of analgesic tolerance can occur at ultra-low doses of NLX and NTX due to the fact that higher doses of these opioid antagonists would begin to antagonize opioid receptors. However, the attenuation of rewarding or addictive properties of opioids by ultra-low-dose NTX is not paradoxical; hence, one expects a continuous suppression of reward as increasing doses NTX are combined with the opioid.

In the conditioned place preference paradigm, although both ultra-low (0.03 and 0.3 ng/kg) and higher (30 ng/kg) NTX doses blocked the acute rewarding effects of oxycodone, an interim dose (3 ng/kg) was without effect (Olmstead et al., 2005 *Psychopharmacology* 181:576-581). Similarly, in a self-administration paradigm, while co-self-administering 10 or 1 pg/kg/infusion both attenuated measures of reinstatement when oxycodone was not available, only the lower dose altered oxycodone's rewarding potency during self-administration (Leri et al., 2005 *Pharmacol Biochem Behav* 82:252-262).

The blunting of opioid rewarding effects by ultra-low-dose NTX first suggests that Gs coupling by MOR can contribute to the rewarding or addictive properties of opioids, possibly by cAMP activation of PKA and subsequent CREB phosphorylation. However, opioid inhibitory effects, such as the proposed disinhibition of VTA dopamine neurons via inhibition of GABA interneurons (Spanagel et al., 1993 *Proc Natl Acad Sci USA* 89:2046-2050), can also contribute to opioid reward. The loss of effect at intermediate NTX doses can indicate such complexities of the neural mechanisms contributing to opioid reward and addiction.

Alternatively, the fact that the attenuation of rewarding effects is diminished as the NTX dose increases could also suggest an upper limit of an effective ultra-low dose range for disrupting the FLNA-MOR interaction and consequent MOR-Gs signaling.

In their entirety, the above results identify a specific C-terminal region of FLNA as the high-affinity binding site of NLX and NTX in their suppression of MOR signaling alterations that result from chronic opioid treatment. This data therefore provides a molecular target for ultra-low-dose NLX through which ultra-low-dose opioid antagonists enhance opioid analgesia and decrease opioid tolerance and dependence. It is thought repeated MOR stimulation can lead to a particular conformation of MOR-FLNA that weakens Gi/o-MOR-FLNA complexes and permits MORs to release to interact with Gs upon subsequent stimulation by morphine. By binding to FLNA, NLX and its analogs prevent this altered MOR-FLNA interaction, thereby preventing the release from the complexes and the resultant altered coupling.

There are multiple signaling consequences of the switch to Gs coupling by MORs chronically exposed to opioids, and each can contribute differently to the various behavioral effects of long-term opioid administration such as analgesic tolerance, physical dependence and the possibility of addiction. This notion can explain the multiple beneficial effects of ultra-low-dose opioid antagonist co-treatment that has been shown to preserve the normal G protein coupling profile of MOR (Wang et al., 2005 *Neuroscience* 135:247-261).

V. Acute Morphine-Induced MOR-Gs Coupling is Prevented by Administration of an Ultra-Low-Dose Opioid Antagonist (NLX/NTX) or a VAKGL-Containing Peptide An acute morphine-induced Go-to-Gs coupling switch in organotypic striatal slice cultures was blocked by co-exposure to ultra-low-dose NLX, NTX or their pentapeptide binding site on FLNA (FIG. 1). Morphine itself (100 µM) caused a complete Go-to-Gs coupling switch by MOR at 5 and 15 minutes of exposure. After 60 minutes of morphine exposure, the switch had resolved and no further Gs coupling was detected.

This finding illustrates that the switch to Gs coupling by MOR is not solely a consequence of chronic morphine, but is instead a dynamic phenomenon occurring acutely after high-dose morphine exposure, perhaps becoming less dynamic and more persistent if opioid exposure is repeated or prolonged. Co-treatment with ultra-low-dose (100 µM) NLX or NTX prevented this acute G protein coupling switch by MOR (FIG. 1B and FIG. 1D).

Figure 1B:
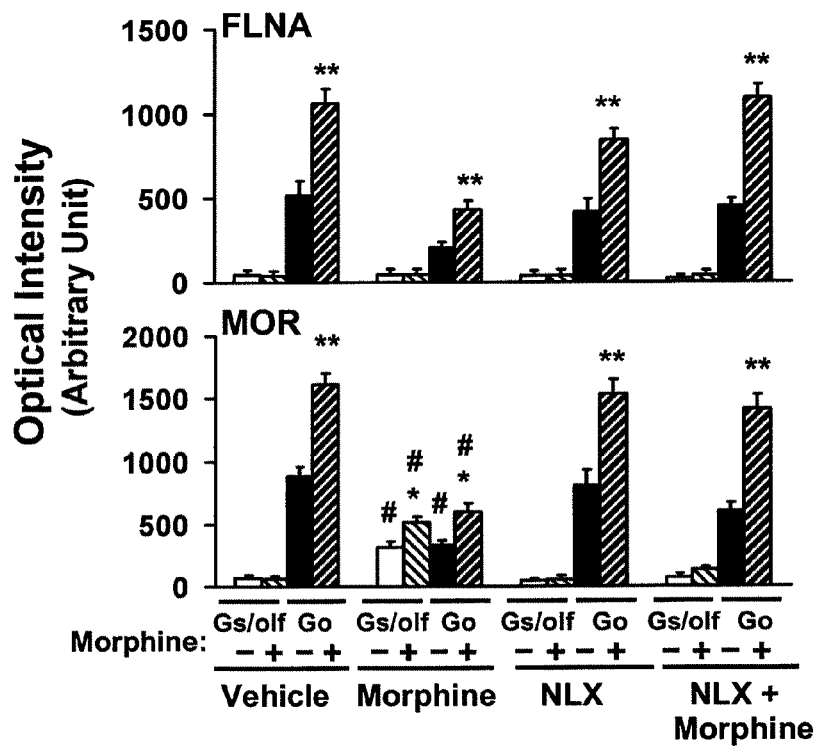
Figure 1C:
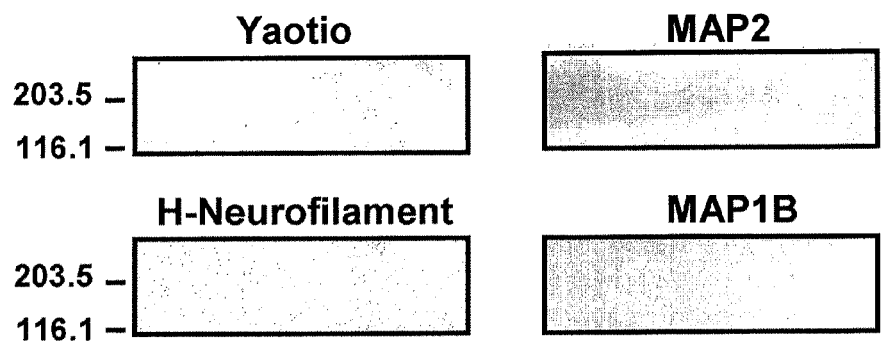

Similarly, pre-treatment with the pentapeptide binding site of NLX or NTX on FLNA (VAKGL (SEQ ID NO:14);

FLNA$_{2561-2565}$)) at 10 µM concentration also completely prevented this acute morphine-induced coupling switch by MOR (FIG. 1B). The control peptide, FLNA$_{2561-2565}$ with one midpoint alanine substitution (VAKGL, SEQ ID NO:12), did not prevent the MOR-Gs coupling observed at 5 and 15 minutes, but mildly preserved Go coupling at 15 minutes, suggesting a weak protective effect at this interim time-point. Exposure to NLX, NTX or either peptide alone without morphine had no effect on MOR coupling. In sum, the only significant differences compared to the vehicle condition for both Go and Gs coupling were the 5 and 15 minute time points for both morphine and morphine+the control peptide (VAAGL (SEQ ID NO:12)) ($p<0.01$ for each).

Acute high-dose morphine causes a transient MOR-Gs coupling that resolves by 1 hour in the organotypic striatal slice cultures. This is the first indication that MOR-Gs coupling occurs acutely and dynamically and is not only a consequence of chronic opioid treatment. To assess the involvement of FLNA in this acute opioid-induced Gs coupling, slices were co-treated with NLX, NTX or FLNA$_{2561-2565}$, their pentapeptide binding site, as a decoy for MOR.

The effects of these treatments were also examined on cAMP-response-element-binding protein (CREB) phosphorylation at $S^{133}$ as a marker of addictive processes, as it has been shown that ultra-low-dose NTX attenuates the acute rewarding effects of opioids (Leri et al., 2005 *Pharmacol Biochem Behav* 82:252-262; Olmstead et al., 2005 *Psychopharmacology* 181:576-581). CREB is activated by phosphorylation at $S^{133}$ by protein kinase A, which itself is activated by cAMP. Hence, increasing levels of cAMP from activation of adenylyl cyclase following MOR-Gs coupling could contribute to the acute rewarding or addictive properties of opiates. A partial mediation of the acute rewarding effects of opiates by Gs signaling could explain the apparent discrepancy that ultra-low-dose NLX or NTX can enhance opioid analgesia, while also attenuating the addictive properties of opioids.

The transient Gs coupling resulting from acute opioid exposure, evident at 5 and 15 minutes of high-dose morphine exposure, is unlikely to represent an acute tolerance/dependence effect as MOR had completely reverted to its native Go coupling by 1 hour of morphine exposure. Instead, it is thought that with strong stimulation, MOR couples to Gs instead of Gi/o but is able to recover via continuous receptor internalization and recycling. With repeated or prolonged MOR stimulation, however, this dynamic cycling from Gs back to Go can become impaired, leading to a persistent Gs coupling, behaviorally manifest as opioid analgesic tolerance and dependence.

Similar to ultra-low-dose NLX's suppression of the chronic morphine-induced coupling switch, the acute morphine-induced coupling switch by MOR can be completely prevented by co-treatment with ultra-low-dose NLX, NTX or their VAKGL-containing peptide binding site on FLNA. As noted above, FLNA peptides presumably bound to NLX, block its prevention of the morphine-induced MOR-Gs coupling by blocking access to full-length FLNA in the tissues. These data led to the hypothesis that the interaction between MOR and FLNA was critical to the G protein coupling switch. It is thought that a particular FLNA-MOR interaction can enable MOR to release from the signaling complex to couple to Gs with subsequent receptor stimulation.

It was found that the pentapeptide FLNA$_{2561-2565}$ itself acts as a decoy for MOR to prevent the MOR-FLNA interaction and subsequent Gs coupling by MOR. This decoy pentapeptide was as effective as NLX or NTX: all three completely blocked the transient switch to Gs coupling by MOR during acute, high-dose morphine exposure.

The present invention suggests that NLX and NTX prevent the MOR-FLNA interaction by binding to FLNA at the approximate site that interacts with MOR, while the decoy pentapeptide prevents this interaction by binding to MOR. If, on the other hand, NLX and NTX block MOR-Gs coupling by changing the conformation of FLNA upon binding and not by direct interference, the decoy would have to be exerting its effects by binding to "itself" in the full-length protein, thus similarly preventing the changed FLNA conformation.

With no evidence that the pentapeptide binds full-length FLNA or aggregates in solution, it is believed that its effects are a result of binding to MOR. Further, this pentapeptide NLX binding site on FLNA appears be the approximate site on this protein that interacts with MOR. Finally, as the peptide binding site can both prevent NLX's protective effects shown in the Examples hereinafter, and mimic NLX's protective effects when used alone in the current study, it is thought that this pentapeptide preferentially binds NLX, but in its absence will interact with MOR.

VI. Acute Morphine-Induced CREB $S^{133}$ Phosphorylation is Prevented by Administration of an Ultra-Low-Dose Opioid Antagonist (NLX/NTX) or a VAKGL-Containing Peptide Acute high-dose morphine (100 µM) produced an activation of CREB by phosphorylation at serine-133 that paralleled the time course of the Gs coupling (FIG. 3). A robust level of pS$^{133}$CREB was detected in striatal tissue from organotypic striatal slice cultures after 5 and 15 minutes of morphine exposure, while only a residual level was detected after 1 hour of morphine exposure. Co-treatment with ultra-low-dose (100 pM) NLX or NTX, or pre-treatment with 10 µM of the VAKGL (SEQ ID NO:14) pentapeptide, the binding site of NLX or NTX on FLNA (FLNA$_{2561-2565}$), virtually abolished this signal. In contrast, pre-treatment with the control peptide VAAGL (SEQ ID NO:12) did not significantly diminish pS$^{133}$CREB levels seen in the morphine only condition. Treatment alone with NLX, NTX or either peptide did not result in pS$^{133}$CREB detection. As with the Gs and Go coupling, only morphine and morphine+the control peptide produced significant differences compared to the vehicle condition ($p<0.01$ for 5 and 15 minute time points and $p<0.05$ for 60 minute time points).

Conclusions

The demonstration that all three co-treatments, NLX, NTX or the decoy pentapeptide also prevented morphine-induced CREB activation (as indicated by ser133 phosphorylation) in these striatal slice cultures can offer a mechanistic explanation for the attenuation of opioid reward and addictive processes by ultra-low-dose NTX.

Found in all cells of the brain, CREB is a transcription factor implicated in addiction as well as learning and memory and several other experience-dependent, adaptive (or maladaptive) behaviors (Carlezon et al., 2005 *Trends Neurosci* 28:436-445). In general, CREB is inhibited by acute opioid treatment, an effect that is completely attenuated by chronic opioid treatment, and activated during opioid withdrawal (Guitart et al., 1992 *J Neurochem* 58:1168-1171). However, a regional mapping study showed that opioid withdrawal activates CREB in locus coeruleus, nucleus accumbens and amygdala but inhibits CREB in lateral ventral tegemental area and dorsal raphe nucleus (Shaw-Luthman et al., 2002 *J Neurosci* 22:3663-3672).

In the striatum, CREB activation has been viewed as a homeostatic adaptation, attenuating the acute rewarding effects of drugs (Nestler, 2001 *Am J Addict* 10:201-217; Nestler, 2004 *Neuropharmacology* 47:24-32). This view is supported by nucleus accumbens overexpression of CREB or a dominant-negative mutant respectively reducing or increasing the rewarding effects of opioids in the conditioned place preference test (Barot et al., 2002 *Proc Natl Acad Sci USA* 99:11435-11440). In conflict with this view, however, reducing nucleus accumbens CREB via antisense attenuated cocaine reinforcement as assessed in self-administration (Choi et al., 2006 *Neuroscience* 137:373-383). Clearly, CREB activation is implicated in addiction, but whether it directly contributes to the acute rewarding effects of drugs or initiates a homeostatic regulation thereof appears less clear.

The several-fold increase in $pS^{133}CREB$ observed here following acute, high-dose morphine can indicate acute dependence rather than acute rewarding effects. However, the transient nature of the MOR-Gs coupling correlating with this CREB activation suggests otherwise. In fact, the correlation of $pS^{133}CREB$ with the Gs coupling by MOR following this acute high-dose morphine exposure, as well as the similar treatment effects on both, suggest that this alternative signaling mode of MOR can contribute to the acute rewarding or addictive effects of opioids. This counterintuitive notion can explain the apparent paradox that ultra-low-dose NTX, while enhancing the analgesic effects of opioids, decreases the acute rewarding or addictive properties of morphine or oxycodone as measured in conditioned place preference or self-administration and reinstatement paradigms.

In considering analgesic tolerance, opioid dependence, and opioid addiction together as adaptive regulations to continued opioid exposure, a treatment that prevents MOR's signaling adaptation of switching its G protein partner can logically attenuate these seemingly divergent behavioral consequences of chronic opioid exposure. However, the acute rewarding effects of opioids are not completely blocked by ultra-low-dose opioid antagonists, suggesting that a MOR-Gs coupling can only partially contribute to the addictive or rewarding effects.

Even though ultra-low-dose NTX blocks the conditioned place preference to oxycodone or morphine (Olmstead et al., 2005 *Psychopharmacology* 181:576-581), its co-self-administration only reduces the rewarding potency of these opioids but does not abolish self-administration outright (Leri et al., 2005 *Pharmacol Biochem Behav* 82:252-262). Nevertheless, it is possible that a direct stimulatory effect on VTA neurons, as opposed to the proposed disinhibition via inhibition of GABA interneurons (Spanagel et al., 1993 *Proc Natl Acad Sci USA* 89:2046-2050), can play some role in opioid reward. Finally, a MOR-Gs coupling mediation of reward, increasing with increasing drug exposure, is in keeping with current theories that the escalation of drug use signifying drug dependence can not indicate a "tolerance" to rewarding effects but instead a sensitization to rewarding effects (Zernig et al., 2007 *Pharmacology* 80:65-119.

In their entirety, sections V and VI above have demonstrated that acute, high-dose morphine causes an immediate but transient switch in G protein coupling by MOR from Go to Gs similar to the persistent switch caused by chronic morphine. Ultra-low-dose NLX or NTX prevent this switch and attenuate the chronic morphine-induced coupling switch by MOR. The transient nature of this acute altered coupling suggests the receptor eventually recovers and couples to its native G protein.

With chronic opioid exposure, the receptor can lose the ability to recover and continue to couple to Gs, activating the adenylyl cyclase/cAMP pathway, upregulating protein kinase A, and phosphorylating CREB as one downstream effector example. The persistently elevated phosphorylated CREB can then shape the expression of responsive genes including those closely related to drug addiction and tolerance. Importantly, the equivalent blockade of Gs coupling and $pS^{133}CREB$ by the NLX and NTX-pentapeptide binding site on FLNA further elucidates the mechanism of action of ultra-low-dose NLX and NTX in their varied effects.

These data further strengthen a mechanistic basis for MOR-Gs coupling through the interaction between FLNA and MOR and that disrupting this interaction, either by NLX/NTX binding to FLNA or via a FLNA peptide decoy for MOR, the altered coupling is prevented, resulting in attenuation of tolerance, dependence and addictive properties associated with opioid drugs.

V. Pharmacophore Determinations

An additional aspect of the invention is a method for selecting a compound for VAKGL-binding activity that preferably also possesses mu opioid receptor agonist activity, from candidate compounds. In this aspect, the aromatic/hydrophobic and hydrogen bond acceptor functions and the distances there between of a candidate compound are determined. A compound that exhibits at least three of the pharmacophores shown in FIGS. 12-27 is selected. A selected VAKGL-binding compound can bind to the VAKGL-binding site of filamin A alone, but is preferably also an agonist at the mu-opioid receptor. A selected compound preferably exhibits at least six of the sixteen pharmacophores, more preferably at least nine of those pharmacophores, and most preferably at least twelve of the sixteen pharmacophores.

A contemplated 4-point or 5-point pharmacophore is generated using screened dual active compounds and available soft ware to build the pharmacophore hypotheses. The screened compounds are typically provided from one or more commercially available compound libraries, using inactive compounds to validate the hypotheses.

Several hundred compounds were screened for their binding affinity to FLNA and their stimulation of MOR at a concentration of 0.1 µM. Five compounds from that original screen showed FLNA affinities of less than 9 pM and concurrent stimulation of MOR by at least 64% at 0.1 µM without more than 23% stimulation of other Go-coupled receptors. Data from that screening for six of the seven compounds are provided below in Table 1. In that Table, the log P value is the logarithm of a compound's partition coefficient between n-octanol and water $[\log(c_{octanol}/c_{water})]$, and is a well established measure of the compound's hydrophilicity. "CLogP" shown in the Table is a calculated LogP value that is obtained using a program copyrighted (1988-2008) by Pomona College and BioByte, Inc. of Claremont, Calif.

TABLE 1

| Compound No. | CLogP | Molecular Weight | FLNA affinity (pM) | Stimulation of MOR at (at 0.1 µM) | Stimulation of other $G_o$-coupled receptors |
|---|---|---|---|---|---|
| 1 | 2.76 | 390.51 | 0.45 | 79% | 19% |
| 2 | 3.53 | 396.56 | 0.64 | 67% | 11% |
| 3 | 3.07 | 415.48 | 0.15 | 78% | 16% |
| 4 | — | 415.20 | — | — | — |
| 5 | 3.01 | 482.57 | 8.65 | 91% | 11% |
| 6 | 1.24 | 398.47 | 0.11 | 91% | 23% |
| 7 | 1.56 | 414.47 | 2.86 | 64% | 21% |
| Controls | | | | | |
| Naltrexone | — | — | 3.9 | — | — |
| DAMGO | — | — | — | 92% | 6% |

Using four of those seven compounds as an initial training set, the set of sixteen 4-point and 5-point pharmacophores were prepared. The active compounds and the pharmacophores that they contain are shown in Table 2, below, wherein the "compound No." for a depicted compound whose structure is shown are the same between Tables 1 and 2.

TABLE 2

Compounds and Pharmacophore Models*

| Compound Structure | Compound No. | Pharmacophore Model of FIG. No. |
|---|---|---|
| [steroid structure with OCH3, CH3, and acetate groups, chiral] | 1 | 14, 16, 21 |
| [polycyclic structure with OH, HO, CH3 groups, chiral] | 2 | 12-27 |
| [structure with OCH3, HO, methylenedioxy, N-CH3, chiral] | 3 | 12-14, 17-23, 27 |
| [methylenedioxy tetrahydroisoquinolinium structure with OH, CH3, tetrahydropyran] | 4 | 12-21, 23-25, 27 |

TABLE 2-continued

Compounds and Pharmacophore Models*

| Compound Structure | Compound No. | Pharmacophore Model of FIG. No. |
|---|---|---|
| [bis-sulfonamide spiro structure with two methoxyphenyl-SO2 groups] | 5 | 12, 14-15, 17-20, 22-27 |
| [methylenedioxy methoxyphenyl tetrahydroisoquinolinium with N,N-dimethyl, iodide] | 6 | 12, 16, 21, 27 |
| [methylenedioxy dimethoxyphenyl tetrahydroisoquinolinium with N,N-dimethyl, iodide] | 7 | 12, 14-15, 25, 27 |

*The indication "1-3" denotes that the compound hits pharmacophores 1, 2 and 3, whereas the indication "1, 3" denotes that the compound hits pharmacophores 1 and 3 only.

EXAMPLES

The present invention is described in the following examples which are set forth to aid in the understanding of the invention, and should not be construed to limit in any way the invention as defined in the claims which follow thereafter.

The experiments described herein were carried out on organotypic striatal slices from male Sprague Dawley rats (200 to 250 g) purchased from Taconic (Germantown, N.Y.). Rats were housed two per cage and maintained on a regular 12-hour light/dark cycle in a climate-controlled room with food and water available ad libitum and sacrificed by rapid decapitation. All data are presented as mean±standard error of the mean. Treatment effects were evaluated by two-way ANOVA followed by Newman-Keul's test for multiple comparisons. Two-tailed Student's t test was used for post hoc pairwise comparisons. The threshold for significance was $p<0.05$.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

Example 1

For identification of NLX-binding protein in MOR immunoprecipitates, four groups of 4 rats were treated twice daily for 7 days with vehicle, NLX (10 ng/kg, s.c.), morphine (10 mg/kg, s.c.), or morphine+NLX. For organotypic brain slice cultures, striata were removed on ice and treated in vitro as described below. All procedures carried out in these protocols are in compliance with the City College of New York IACUC on the use and care of animals.

To identify the NLX-binding protein in MOR immunoprecipitates, MOR and its associated scaffolding proteins and G proteins were immunopurified together using anti-Gαs/olf or -Gαo antibodies that were immobilized to prevent interference from immunoglobulins. Anti-Gα antibodies (Santa Cruz Biotechnology, Santa Cruz, Calif.) were covalently cross-linked to protein A conjugated resin in a Seize-X protein A immunoprecipitation kit (Pierce-ENDOGEN, Rockford, Ill.) according to manufacturer's instructions. MOR-G protein-scaffolding protein complexes in solubilized brain lysate were first isolated by immunoprecipitation in which 200 μg solubilized brain membrane extract from striatum was incubated with immobilized anti-Gα-protein A-resin at 4° C. overnight.

After centrifugation and three washes with phosphate-free Kreb's-Ringer (pH 7.4) containing mixtures of protease and protein phosphatase inhibitors at 4° C., the MOR-G protein-scaffolding protein complexes were eluted with 200 μl of neutral pH gentle antigen elution buffer, diluted 5-fold with immunoprecipitation buffer, and immunoprecipitated with anti-MOR at 4° C. for 4 hours followed by 50 μl protein A/G-conjugated beads (Santa Cruz Biotechnology) for 2 hours. The immunoprecipitates containing MOR-G protein-scaffolding protein complexes were collected by centrifugation and washed twice with phosphate-free Kreb's-Ringer. The washed immunocomplex was re-suspended in 75 μl phosphate-free Kreb's-Ringer and solubilized by combining with 75 μl of 2×PAGE sample preparation buffer (62.5 mM Tris-HCl, pH6.8; 20% glycerol, 4% SDS; 10% 2-mercaptoethanol, 0.1% bromophenol blue) and boiled for 5 minutes.

The levels of selective MOR-associated scaffolding proteins were determined by Western blotting using specific antibodies directed against various cytoskeletal and scaffolding proteins including FLNA, MAP1B and yaotio.

To confirm FLNA as the high-affinity target of NLX, [$^3$H] NLX binding to the human melanoma cell line M2 and its subclone A7 was assessed. The M2 subclone lacks FLNA and MOR and its subclone A7 is stably transfected with human FLNA cDNA (obtained from Drs. Stossel and Ohta at Harvard Medical School).

Membranes prepared from A7 cells (50 μg) were incubated in binding medium consisting of 50 mM Tris HCl, pH 7.5; 100 mM NaCl; and protease and protein phosphatase inhibitors with 500 pM [$^3$H]NLX for 30 minutes at 37° C. Total incubation volume was 500 μl. Non-specific binding was defined by 1 μM NTX. The parent M2 cells that do not express FLNA served as a negative control. Reactions were terminated by rapid filtration through GF/B membranes under vacuum. The filters were washed twice with 5 ml ice-cold binding medium, and [$^3$H]NLX retained on the filters was measured by liquid scintillation spectrometry.

Example 2

To determine the NLX binding site on FLNA, various overlapping peptides encoding the c-terminal section of FLNA were used to compete for [$^3$H]NLX binding to FLNA using either A7 cell membranes or purified FLNA from A7 or SK-N-MC cells. Peptides were prepared by Sigma-Genosys (The Woodlands, Tex.). The reaction mixture consisted of 100 μg A7 membranes or 2 μg purified FLNA, 500 pM [$^3$H]NLX, and 10 μM of either $FLNA_{2550-2560}$, $FLNA_{2556-2565}$, $FLNA_{2561-2570}$, $FLNA_{2566-2575}$ or $FLNA_{2576-2581}$ in 500 μl binding medium. The reaction was carried out at 37° C. for 30 minutes and terminated by rapid filtration through GF/B membranes under vacuum. The filters were washed twice with 5 ml ice-cold binding medium, and [$^3$H]NLX retained on the filters was measured by liquid scintillation spectrometry.

Example 3

To determine the essential amino acid residue(s) within the NLX-interacting pentapeptide, four additional pentapeptides, each with one amino acid residue replaced by alanine, were used along with the correct $FLNA_{2561-2565}$ pentapeptide to compete for [$^3$H]NLX binding to FLNA using 100 μg A7 cell membranes. Peptides were generated by Sigma-Genosys. The reaction mixture consisted of 500 pM [$^3$H]NLX, 100 μg A7 membranes, and 10 μM pentapeptide [AAKGL, (SEQ ID NO:13); VAKGL (SEQ ID NO:14); VAAGL (SEQ ID NO:12); VAKAL (SEQ ID NO:15) or VAKGA (SEQ ID NO:16)] in 500 μl binding medium. The reaction was conducted at 37° C. for 30 minutes and terminated by rapid filtration through GF/B membranes under reduced pressure. The filters were washed twice with 5 ml ice-cold binding medium, and [$^3$H]NLX retained on the filters was measured by liquid scintillation spectrometry.

Example 4

In this set of studies, the rat brain slice organotypic culture methods were modified from those published previously (Adamchik et al., 2000 *Brain Res Protoc* 5:153-158; Stoppini et al., 1991 *J Neurosci Methods* 37:173-182). Striatal slices (200 μM thickness) were prepared using a McIlwain tissue chopper (Mickle Laboratory Engineering Co., Surrey, UK). Slices were carefully transferred to sterile, porous culture inserts (0.4 μm, Millicell-CM) using the rear end of a glass Pasteur pipette. Each culture insert unit contained 2 slices and was placed into one well of the 12-well culture tray. Each well contain 1.5 ml of culture medium composed of 50% MEM with Earl's salts, 2 mM L-glutamine, 25% Earl's balanced salt solution, 6.5 g/l D-glucose, 20% fetal bovine serum, 5% horse serum, 25 mM HEPES buffer, 50 mg/ml streptomycin and 50 mg/ml penicillin. The pH value was adjusted to 7.2 with HEPES buffer.

Cultures were first incubated for 2 days to minimize the impact of injury from slice preparation. Incubator settings throughout the experiment were 36° C. with 5% $CO_2$. To induce tolerance, culture medium was removed and the culture insert containing the slices was gently rinsed twice with warm (37° C.) phosphate-buffered saline (pH 7.2) before incubation in 0.1% fetal bovine serum-containing culture medium with 100 μM morphine for 1 hour twice daily (at 9-10 AM and 3-4 PM) for 7 days.

To assess the effect of ultra-low-doses of NLX on the chronic morphine-induced signaling switch, some slices were exposed to 100 μM morphine plus 10 pM NLX.

To determine whether NLX's protective effect occurs by binding to FLNA at $FLNA_{2561-2565}$, brain slices were incubated with morphine plus NLX and with the addition of 10 μM $FLNA_{2550-2560}$, $FLNA_{2561-2570}$, or $FLNA_{2566-2575}$.

Slices were returned to culture medium with normal serum after each drug exposure. Tissues were harvested 16 hours after the last drug exposure by centrifugation.

For determination of MOR-G protein coupling, slices were homogenated to generate synaptic membranes. Synaptic membranes (400 μg) were incubated with either 1 μM morphine or Kreb's-Ringer solution for 10 minutes before solubilization in 250 μl of immunoprecipitation buffer (25 mM HEPES, pH 7.5; 200 mM NaCl, 1 mM EDTA, 50 μg/ml leupeptin, 10 μg/ml aprotinin, 2 μg/ml soybean trypsin inhibitor, 0.04 mM PMSF and mixture of protein phosphatase inhibitors). Following centrifugation, striatal membrane lysates were immunoprecipitated with immobilized anti-Gαs/olf or -Gαo conjugated with immobilized protein G-agarose beads. The level of MOR in anti-Gαs/olf or -Gαo immunoprecipitates was determined by Western blotting using specific anti-MOR antibodies.

To measure the magnitude of MOR-mediated inhibition of cAMP production, brain slices were incubated with Kreb's-Ringer (basal), 1 μM DAMGO, 1 μM forskolin or 1 μM DAMGO+1 μM forskolin for 10 minutes at 37° C. in the presence of 100 μM of the phosphodiesterase inhibitor IBMX. Tissues were homogenized by sonication and protein precipitated with 1M TCA. The supernatant obtained after centrifugation was neutralized using 50 mM Tris, pH 9.0. The level of cAMP in the brain lysate was measured by a CAMP assay kit (PerkinElmer Life Science, Boston) according to manufacturer's instructions.

Example 5

Rat brain slice organotypic culture methods were carried out as in Example 4 above. Studies were designed to assess the effect of a decoy pentapeptide fragment of filamin A, $FLNA_{2561-2565}$ (VAKGL (SEQ ID NO:14)) and ultra-low-dose NLX or NTX on acute morphine-induced MOR-Gs coupling. Culture medium was removed and the culture insert containing the slices was gently rinsed twice with warm (37° C.) phosphate-buffered saline (pH 7.2) before incubation in 0.1° fetal bovine serum-containing culture medium for 2 hours.

To assess the effect of ultra-low-dose of NLX or NTX on the acute morphine-induced signaling switch, some slices were exposed to 100 μM morphine plus 100 pM NLX or NTX. To determine whether NLX's effect can be mimicked by the site on FLNA that interacts with MOR, brain slices were incubated with morphine plus 10 μM VAKGL (SEQ ID NO:14) or control pentapeptide, VAAGL (SEQ ID NO:12).

Tissues were harvested 5, 15 or 60 minutes after the drug exposure by centrifugation. For determination of MOR-G protein coupling, slices were homogenated to generate synaptic membranes and cytosolic fractions. Synaptic membranes (400 μg) were then solubilized with 0.5% digitonin/0.2% sodium cholate/0.5% NP-40 in 250 μl of immunoprecipitation buffer (25 mM HEPES, pH 7.5; 200 mM NaCl, 1 mM EDTA, 50 μg/ml leupeptin, 10 μg/ml aprotinin, 2 μg/ml soybean trypsin inhibitor, 0.04 mM PMSF and mixture of protein phosphatase inhibitors). Following centrifugation, striatal membrane lysates were immunoprecipitated with immobilized anti-Gαs/olf or -Gαo (Santa Cruz) conjugated with immobilized protein A-agarose beads (Pierce-Endogen). The level of MOR in anti-Gαs/olf or -Gαo immunoprecipitates was determined by Western blotting using specific anti-MOR antibodies.

Example 6

To assess whether acute high-dose morphine induces CREB activation and whether co-treatment with ultra-low-dose NLX, NTX or the decoy pentapeptide alter it, the level of protein kinase A-phosphorylated CREB, $pS^{133}$-CREB, was assessed in cytosolic and nucleus fractions generated as described above from striatal slices. CREB in the solubilized cytosol and nucleus was immunoprecipitated with an anti-CREB antibody (Santa Cruz) and the level of $pS^{133}$-CREB was then determined by Western blotting using a specific antibody directed against $pS^{133}$-CREB (Santa Cruz).

The foregoing description and the examples are intended as illustrative and are not to be taken as limiting. Still other variations within the spirit and scope of this invention are possible and will readily present themselves to those skilled in the art.

What is claimed is:

1. An isolated polypeptide or analog thereof containing up to 50 amino acid residues consisting of the amino acid sequence W-(Val Thr Gly Pro Arg Leu Val Ser Asn His Ser Leu His Glu Thr Ser Ser Val Phe Val Asp Ser Leu Thr Lys Ala Thr Cys Ala Pro Gln His Gly Ala Pro Gly Pro Gly Pro Ala Asp Ala Ser Lys Val)$_n$ Val Ala Xaa Gly Leu (Gly Leu Ser Lys Ala Tyr Val Gly Gln Lys Ser Ser Phe Thr Val Asp Cys Ser Lys Ala Gly Asn Asn Met Leu Leu Val Gly Val His Gly Pro Arg Thr Pro Cys Glu Glu Ile Leu Val Lys His Val Gly)$_m$-Y SEQ ID NO: 17 wherein W is hydrogen or a $C_1$-$C_{20}$ acyl group;

Y is a hydroxyl group, an amino group, or substituted amino group represented by —$NR^1R^2$, wherein $R^1$ and $R^2$ are independently selected from the group consisting of a hydrido, a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or $R^1$ and $R^2$ together with the depicted nitrogen atom form a 5- to 8-membered ring containing zero or one additional heteroatom that is oxygen, nitrogen, or sulfur;

Xaa is an amino acid residue;

n and m are each independently zero or 1, wherein when n is zero, amino acid residues within the parentheses are absent and when n is 1, up to 45 residues of the parenthesized amino acid sequence are present, with the proviso that when one of the residues within the parentheses is present, each residue to the carboxy-terminal side of said residue is also present in the sequence shown, and when m is zero, amino acid residues within the parentheses are absent, and when m is 1, up to 45 residues of the parenthesized amino acid sequence are present, with the proviso that when one of the residues within the parentheses is present, each residue to the amino-terminal side of said residue is also present in the sequence shown.

2. The isolated polypeptide or analog thereof according to claim 1, wherein Xaa is a basic amino acid residue.

3. The isolated polypeptide or analog thereof according to claim 2, wherein Xaa is lysine.

4. The isolated polypeptide or analog thereof according to claim 1, wherein W is hydrogen, Y is a hydroxyl group and Xaa is lysine.

5. The isolated polypeptide or analog thereof according to claim 1 that binds to a VAKGL-binding compound, wherein the binding affinity of said VAKGL-binding compound for said peptide is about $5e^{-10}$ M to about $5e^{-12}$ M.

6. The isolated polypeptide or analog thereof according to claim 5, wherein said binding affinity is about $5e^{-11}$ M.

7. The isolated polypeptide or analog thereof according to claim 5, wherein said VAKGL-binding compound is naloxone or naltrexone.

8. The isolated polypeptide or analog thereof according to claim 1 that binds to VAKGL-binding compound, said VAKGL-binding compound also binds to a mu opioid receptor, wherein the binding affinity of said VAKGL-binding compound is about 20-fold greater for said peptide than for said mu-opioid receptor.

9. The isolated polypeptide or analog thereof according to claim 8, wherein said VAKGL-binding compound is ultra-low-dose naloxone or naltrexone.

10. An isolated polypeptide consisting of the amino acid sequence selected from the group consisting of SEQ. ID. NO:3, SEQ. ID. NO:5, SEQ. ID. NO:6, SEQ. ID. NO:7, SEQ. ID. NO:8, SEQ. ID. NO:9, SEQ. ID. NO:10, SEQ. ID. NO:11 and SEQ. ID. NO:14.

11. A method for screening a candidate opioid antagonist binding to an isolated polypeptide or analog thereof (a candidate VAKGL-binding compound) that contains up to 50 amino acid residues consisting of the amino acid sequence W-(Val Thr Gly Pro Arg Leu Val Ser Asn His Ser Leu His Glu Thr Ser Ser Val Phe Val Asp Ser Leu Thr Lys Ala Thr Cys Ala Pro Gln His Gly Ala Pro Gly Pro Gly Pro Ala Asp Ala Ser Lys Val)$_n$ Val Ala Xaa Gly Leu (Gly Leu Ser Lys Ala Tyr Val Gly Gln Lys Ser Ser Phe Thr Val Asp Cys Ser Lys Ala Gly Asn Asn Met Leu Leu Val Gly Val His Gly Pro Arg Thr Pro Cys Glu Glu Ile Leu Val Lys His Val Gly)$_m$-Y SEQ ID NO: 17 wherein W is hydrogen or a $C_1$-$C_{20}$ acyl group;

Y is a hydroxyl group, an amino group, or substituted amino group represented by —$NR^1R^2$, wherein $R^1$ and $R^2$ are independently selected from the group consisting of a hydrido, a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or $R^1$ and $R^2$ together with the depicted nitrogen atom form a 5- to 8-membered ring containing zero or one additional heteroatom that is oxygen, nitrogen, or sulfur;

Xaa is an amino acid residue;

n and m are each independently zero or 1, wherein when n is zero, amino acid residues within the parentheses are absent and when n is 1, up to 45 residues of the parenthesized amino acid sequence are present, with the proviso that when one of the residues within the parentheses is present, each residue to the carboxy-terminal side of said residue is also present in the sequence shown, and when m is zero, amino acid residues within the parentheses are absent, and when m is 1, up to 45 residues of the parenthesized amino acid sequence are present, with the proviso that when one of the residues within the parentheses is present, each residue to the amino-terminal side of said residue is also present in the sequence shown, comprising the steps of:

(a) contacting said candidate VAKGL-binding compound with said polypeptide;

(b) maintaining said contact for a time period sufficient for said candidate VAKGL-binding compound and said polypeptide to bind to each other; and (c) determining the binding of said candidate VAKGL-binding compound to said polypeptide.

12. The method according to claim 11, wherein Xaa is a basic amino acid residue.

13. The method according to claim 11, wherein said isolated polypeptide is SEQ. ID. NO:14 (Val-Ala-Lys-Gly-Leu).

14. The isolated polypeptide or analog thereof according to claim 1, wherein said isolated polypeptide is SEQ. ID. NO:14 (Val-Ala-Lys-Gly-Leu).

15. A method for determining the ability of an isolated polypeptide to interfere with candidate VAKGL-binding-compound-induced inhibition of the interaction of a mu opioid receptor coupling to a Gs protein that contains a Gα subunit, wherein said Gα subunit is present as Gα inhibitory subunit (Gαi/o) or Gα stimulatory subunit (Gαs), comprising the steps of:

(a) admixing an opioid agonist and said candidate VAKGL-binding compound with mammalian cells that contain said mu-opioid receptor and filamin A (FLNA) in their native conformations or relative orientations, said opioid agonist being present in an agonist effective amount and/or being administered in a repeated, chronic manner and said VAKGL-binding compound being present in an FLNA-binding effective amount;

(b) admixing an isolated polypeptide or analog thereof with said mammalian cells, said isolated polypeptide or analog thereof containing up to 50 amino acid residues consisting of the amino acid sequence W-(Val Thr Gly Pro Arg Leu Val Ser Asn His Ser Leu His Glu Thr Ser Ser Val Phe Val Asp Ser Leu Thr Lys Ala Thr Cys Ala Pro Gln His Gly Ala Pro Gly Pro Gly Pro Ala Asp Ala Ser Lys Val)$_n$ Val Ala Xaa Gly Leu (Gly Leu Ser Lys Ala Tyr Val Gly Gln Lys Ser Ser Phe Thr Val Asp Cys Ser Lys Ala Gly Asn Asn Met Leu Leu Val Gly Val His Gly Pro Arg Thr Pro Cys Glu Glu Ile Leu Val Lys His Val Gly)$_m$-Y SEQ ID NO: 17 wherein W is hydrogen (hydrido) or a $C_1$-$C_{20}$ acyl group;

Y is a hydroxyl group, an amino group, or substituted amino group represented by —$NR^1R^2$, wherein $R^1$ and $R^2$ are independently selected from the group consisting of a hydrido, a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or $R^1$ and $R^2$ together with the depicted nitrogen atom form a 5- to 8-membered ring containing zero or one additional heteroatom that is oxygen, nitrogen, or sulfur;

Xaa is an amino acid residue;

n and m are each independently zero or 1, wherein when n is zero, amino acid residues within the parentheses are absent and when n is 1, up to 45 residues of the parenthesized amino acid sequence are present, with the proviso that when one of the residues within the parentheses is present, each residue to the carboxy-terminal side of said residue is also present in the sequence shown, and when m is zero, amino acid residues within the parentheses are absent, and when m is 1, up to 45 residues of the parenthesized amino acid sequence are present, with the proviso that when one of the residues within the parentheses is present, each residue to the amino-terminal side of said residue is also present in the sequence shown; and c) determining the presence of candidate VAKGL-binding-compound-induced inhibition by analysis of the presence or the absence of said Gαs subunit, after MOR stimulation, wherein said presence indicates a failure of said polypeptide to interfere with candidate VAKGL-binding-compound-induced inhibition of the interaction of said mu opioid receptor with said Gs protein.

16. The method according to claim 15, wherein determining inhibition of the interaction of said mu opioid receptor with said Gs protein further comprises measuring:

(a) the levels of cAMP production, which indicate stimulation of adenylyl cyclase by Gαs or Gβγ; and (b) the levels or presence of $S^{133}$ phosphorylation of CREB (CREB activation via phosphorylation by cAMP-dependent protein kinase A (PKA).

17. The method according to claim 15, wherein said isolated polypeptide is SEQ. ID. NO:14 (Val-Ala-Lys-Gly-Leu).

18. A method for inhibiting the interaction of a mu-opioid receptor coupling to a Gs protein that contains a Gα subunit, wherein said Gα subunit is present as Gα inhibitory (Gαi/o) subunit or Gα stimulatory subunit (Gαs), comprising the steps of:

(a) admixing a VAKGL-binding compound with mammalian cells that contain said mu-opioid receptor and filamin A (FLNA) in their native conformations or relative orientations, said VAKGL-binding compound being present in an agonist effective amount and/or being administered in a repeated, chronic manner;

(b) admixing an FLNA-binding effective amount of an isolated polypeptide or analog thereof with said mammalian cells, said isolated polypeptide or analog thereof containing up to 50 amino acid residues consisting of the amino acid sequence W-(Val Thr Gly Pro Arg Leu Val Ser Asn His Ser Leu His Glu Thr Ser Ser Val Phe Val Asp Ser Leu Thr Lys Ala Thr Cys Ala Pro Gln His Gly Ala Pro Gly Pro Gly Pro Ala Asp Ala Ser Lys Val)$_n$ Val Ala Xaa Gly Leu (Gly Leu Ser Lys Ala Tyr Val Gly Gln Lys Ser Ser Phe Thr Val Asp Cys Ser Lys Ala Gly Asn Asn Met Leu Leu Val Gly Val His Gly Pro Arg Thr Pro Cys Glu Glu Ile Leu Val Lys His Val Gly)$_m$-Y SEQ ID NO: 17 wherein W is hydrogen or a $C_1$-$C_{20}$ acyl group;

Y is a hydroxyl group, an amino group, or substituted amino group represented by —NR$^1$R$^2$, wherein R$^1$ and R$^2$ are independently selected from the group consisting of a hydrido, a $C_1$-$C_6$-hydrocarbyl group, an amino $C_1$-$C_6$-hydrocarbyl group, a hydroxy $C_1$-$C_6$-hydrocarbyl group, an aryl group, an ar-$C_1$-$C_6$-hydrocarbyl group, and a $C_1$-$C_{20}$ acyl group, or R$^1$ and R$^2$ together with the depicted nitrogen atom form a 5- to 8-membered ring containing zero or one additional heteroatom that is oxygen, nitrogen, or sulfur;

Xaa is an amino acid residue;

n and m are each independently zero or 1, wherein when n is zero, amino acid residues within the parentheses are absent and when n is 1, up to 45 residues of the parenthesized amino acid sequence are present, with the proviso that when one of the residues within the parentheses is present, each residue to the carboxy-terminal side of said residue is also present in the sequence shown, and when m is zero, amino acid residues within the parentheses are absent, and when m is 1, up to 45 residues of the parenthesized amino acid sequence are present, with the proviso that when one of the residues within the parentheses is present, each residue to the amino-terminal side of said residue is also present in the sequence shown; and (c) determining said inhibition by analysis of the presence or the absence of said Gαs subunit, wherein the absence of said Gαs subunit indicates inhibition of the interaction of said mu opioid receptor with said Gs protein.

19. The method according to claim 18, wherein determining inhibition of the interaction of said mu opioid receptor with said Gs protein further comprises measuring:

(c) the levels of cAMP production, which indicate stimulation of adenylyl cyclase by Gαs or Gβγ; and (d) the levels or presence of S$^{133}$ phosphorylation of CREB (CREB activation via phosphorylation by cAMP-dependent protein kinase A (PKA).

20. The method according to claim 18, wherein said isolated polypeptide is SEQ. ID. NO:14 (Val-Ala-Lys-Gly-Leu).

* * * * *